US009131949B2

(12) United States Patent
Coleman et al.

(10) Patent No.: US 9,131,949 B2
(45) Date of Patent: Sep. 15, 2015

(54) SYSTEM AND METHOD FOR ASSESSING LITHOTRIPSY

(75) Inventors: Andrew Coleman, London (GB); Fiammetta Fedele, Southampton (GB); Timothy Grant Leighton, Southampton (GB)

(73) Assignees: GUYS AND ST. THOMAS'S NHS FOUNDATION TRUST, London (GB); UNIVERSITY OF SOUTHAMPTON, Southhampton (GB)

(*) Notice: Subject to any disclaimer, the term of this patent is extended or adjusted under 35 U.S.C. 154(b) by 1220 days.

(21) Appl. No.: 12/415,733

(22) Filed: Mar. 31, 2009

(65) Prior Publication Data

US 2010/0249671 A1  Sep. 30, 2010

(51) Int. Cl.
*A61B 17/225* (2006.01)
*A61B 17/22* (2006.01)
*A61B 19/00* (2006.01)
*A61B 17/00* (2006.01)

(52) U.S. Cl.
CPC ......... *A61B 17/225* (2013.01); *A61B 17/22029* (2013.01); *A61B 19/56* (2013.01); *A61B 2017/0011* (2013.01); *A61B 2017/00128* (2013.01)

(58) Field of Classification Search
CPC .......... A61B 17/22029; A61B 17/225; A61B 19/56; A61B 2017/0011; A61B 2017/00128
USPC ........................... 600/459, 437, 438; 601/2, 4
See application file for complete search history.

(56) References Cited

U.S. PATENT DOCUMENTS

| 4,023,175 | A  | * | 5/1977  | Brown et al. ................. 342/179 |
| 5,358,466 | A  | * | 10/1994 | Aida et al. ........................ 601/4 |
| 6,076,005 | A  | * | 6/2000  | Sontag et al. ................. 600/413 |
| 7,687,039 | B2 | * | 3/2010  | Laugharn et al. ............. 422/128 |
| 7,785,276 | B2 | * | 8/2010  | Bohris ............................... 601/2 |

OTHER PUBLICATIONS

Leighton et al., "The Development of a Passive Acoustic Device for Monitoring the Effectiveness of Shockwave Lithotripsy in Real Time", Hydroacoustics, vol. 11, 2008, pp. 159-180.*
Fedele et al., "Development of a new diagnostic sensor for Extracorporeal Shock-Wave Lithotripsy", Journal of Physics: Conference Series 1, Advanced Metrology for Ultrasound in Medicine, 2004, pp. 134-139.*
Fedele et al., An Ultrasound-Based Passive Monitoring System for ESWL, Proceedings of the Institute of Acoustics, vol. 28, Pt. 1, 2006, pp. 770-773.*
Fedele et al., "A New Sensor for Detecting and Characterising Acoustic Cavitation In Vivo during ESWL", Proceedings of the Institute of Acoustics, vol. 26, Pt.2, 2004, pp. 422-432.*

(Continued)

*Primary Examiner* — Katherine Fernandez
(74) *Attorney, Agent, or Firm* — Cooper & Dunham LLP

(57) ABSTRACT

An apparatus, method and system for classifying a shockwave is described, particularly for use in an Extracorporeal Shockwave Lithotripsy (SWL) system. The method for classifying a shockwave generated and directed towards a stone in an extracorporeal shockwave lithotripsy treatment comprises receiving an acoustic signal at a passive unfocused acoustic sensor, determining whether at least one characteristic of the received acoustic emissions exceeds a respective pre-determined threshold value, and classifying the shockwave as effective or ineffective in dependence upon said determination. A method for predicting the outcome of an SWL treatment is also described.

16 Claims, 11 Drawing Sheets

(56) References Cited

OTHER PUBLICATIONS

Cunningham et al., "Characterising in vivo acoustic cavitation during lithotripsy with time-frequency methods", Acoustics Bulletin, Sep./Oct. 2001, pp. 10-16.*

Leighton et al., "Clinical Studies of Real-Time Monitoring of Lithotripter Performance Using Passive Acoustic Sensors", AIP Conference Proceedings, vol. 1049, Apr. 17-18, 2008, pp. 256-277.*

Leighton et al., "A Passive Acoustic Device for Real-time Monitoring of the Efficacy of Shockwave Lithotripsy Treatment", Ultrasound in Med. & Biol., vol. 34, No. 10, 2008, pp. 1651-1665.*

* cited by examiner

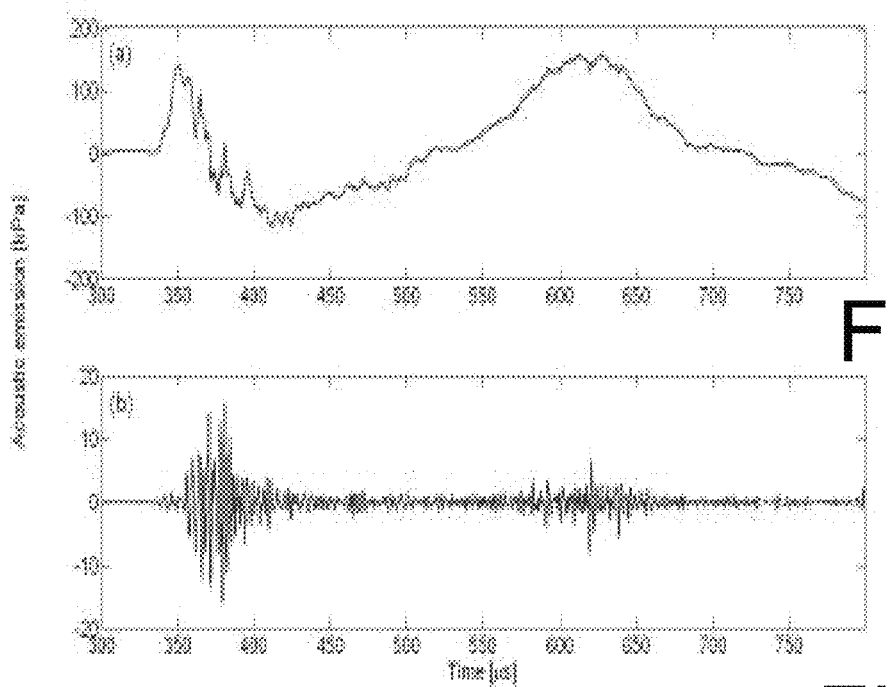
FIG. 7a
FIG. 7b
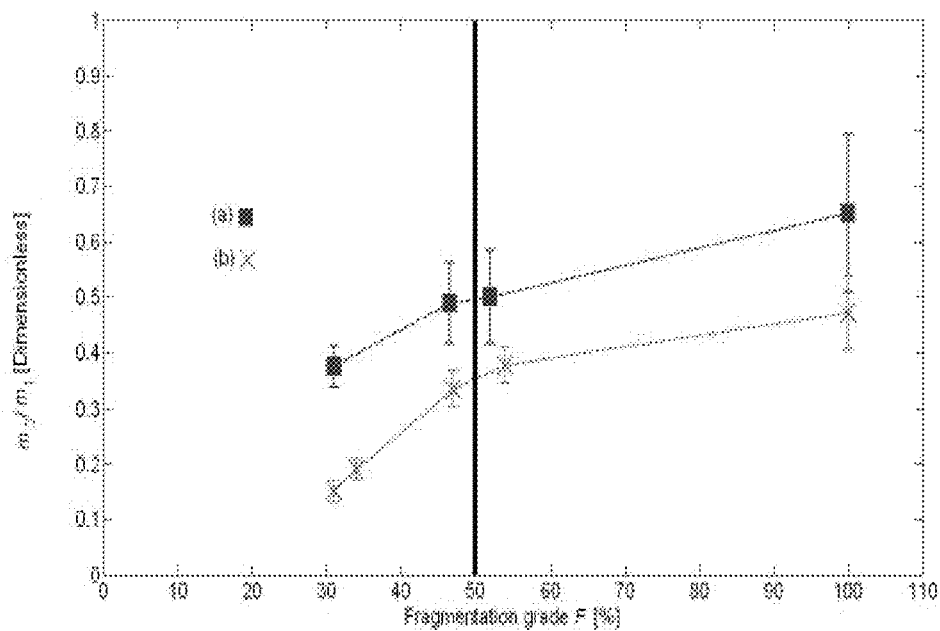
FIG. 10

| ID | Delay [μs] | $m_1$ [mV] | $m_2/m_1$ | $t_c$ [μs] | $\Delta m_1/\Delta shock$ [mV/shock] | $\Delta m_2/\Delta shock$ [mV/shock] | $\Delta t_c/\Delta shock$ [μs/shock] | X-ray assessment | First Opinion |
|---|---|---|---|---|---|---|---|---|---|
| LitA | 283 | 70 | 0.72 | 170 | 0.00 | 0.00 | 0.02 | B | B |
| LitB | 280 | 78 | 0.37 | 165 | 0.00 | 0.00 | 0.01 | NB | B |
| LitC | 310 | 356 | 0 | 0 | 0.02 | N/A | N/A | NB | NB |
| LitD | 276 | 145 | 0.25 | 320 | 0.00 | 0.00 | 0.02 | NB | N/A |
| LitE | 287 | 267 | 0.43 | 204 | 0.03 | 0.01 | 0.01 | B | B |
| LitF | 257 | 477 | 0.22 | 228 | -0.02 | -0.01 | -0.01 | NB | NB |

SYSTEM AND METHOD FOR ASSESSING LITHOTRIPSY

FIELD OF THE INVENTION

The present application relates to an apparatus, method and system for classifying a shockwave, particularly in an Extracorporeal Shockwave Lithotripsy (SWL or ESWL) system.

BACKGROUND OF THE INVENTION

In the course of a number of diseases such as renal, ureteric, salivary duct and gall stone disease, patients may develop hard deposits, known as 'stones'. One method of treating these stones is Extracorporeal Shockwave Lithotripsy (SWL or ESWL). This technique uses acoustic shockwaves generated outside of the body to fragment the stones to a size sufficiently small that they can be passed normally through the body, or so that they can be dissolved using drugs. Several mechanisms are likely contributors to stone fragmentation during SWL. These can be broadly divided into direct stress and cavitation. Direct stress refers to the impact of the shock wave on the stone and the subsequent evolution of stress inside the stone (e.g. spallation, and the formation of shear waves by the incident shock squeezing the stone and the interaction of internal waves in the stone with the surface). Cavitation refers to the growth and collapse of bubbles, for example in the urine surrounding the stone, as a result of the shock from the SWL device. SWL is presently used for the non-invasive treatment of 90% of all kidney stones. However, this method of treatment has a number of associated limitations.

The success of an SWL treatment is currently assessed using ultrasound or X-ray fluoroscopy interrogation. However, it is extremely difficult for an operator to determine whether a stone has been fragmented based on the images produced using such methods, partly because the fragments of a treated stone may stick together following a treatment. Furthermore, the assessment cannot be carried out in real time, for example during the treatment. As a result, SWL treatments tend to follow a 'one size fits all' regimen of, typically, 3000 shocks. As each shock will result in some collateral damage to the surrounding soft tissues, this situation will tend to result in unnecessary damage in patients who might require fewer shocks. In some situations where the treatment has been ineffective, the collateral damage may have been sustained with no benefit to the patient, who will then require repeat or alternative treatment; retreatment rates are currently at 30-50%. Finally, the use of active X-ray fluoroscopy radiation or acoustic waves also exposes the patient to further radiation, in addition to that required for the SWL treatment.

These problems arise largely because it is difficult to align the focus of the lithotripter acoustic beam directly towards the stone, and the performance of the treatment system therefore depends on the size and location of the stone. The alignment, in the absence of a real-time monitoring method, cannot be checked during the treatment unless the treatment is stopped for intermittent check using X-rays or ultrasound. If the stones moves out of the focus during treatment, then in the absence of a real-time monitoring method this would not be detected unless the treatment were stopped.

It is an object of the present invention to mitigate the problems outlined above.

DEFINITIONS

'Stone' is defined for the purpose of this patent application as a deposit, which may be calciferous, crystalline, proteic or fatty in nature, which may be associated with renal, ureteric, salivary duct and gall stone diseases.

'Effective' shockwaves are defined for the purpose of this patent application as those generated shockwaves which contribute, by causing damage to a stone, to any eventual fragmentation of a stone".

'Ineffective' shockwaves would not contribute to such fragmentation.

A 'successful treatment' is defined for the purpose of this patent application as a course of shockwave treatment for which at least about 50% of the generated shockwaves are determined to be 'effective'. This does not necessarily mean that the stone is completely fragmented or that further treatment is not required. As will be described below, this threshold value of about 50% is determined from statistical analysis of test cases of classifying shockwaves using the method of the present invention compared to results of respective x-ray assessments.

The phrase "passive acoustic signal" refers to the acoustic field generated as a result of the interaction between the incident lithotripter shock wave, the tissue and the stone. This may contain energy from a number of sources, including reflection of the incident lithotripter shock wave from the stone, cavitation, and waves generated in the stone as a result (directly or indirectly) of the incident shock lithotripter shock wave.

STATEMENTS OF THE INVENTION

According to one aspect of the present invention, there is provided an assessment method for classifying a shockwave generated and directed towards a stone in an extracorporeal shockwave lithotripsy treatment, the method including receiving the a passive acoustic signal at a passive unfocused acoustic sensor following generation of the lithotripter shockwave, determining whether at least one characteristic of the received passive acoustic signal exceeds a respective predetermined threshold value and classifying the shockwave as effective or ineffective in dependence upon said determination.

By using this method, the operator is able to monitor whether a shockwave has been 'on target' and whether it has resulted in cavitation. The operator may then stop the treatment if necessary, and may take the opportunity to retarget the SWL device, for example to reduce the number of ineffective shockwaves to which a patient may otherwise be subjected, thereby causing collateral damage. Furthermore, the operator can then make the necessary modifications to the focus of the acoustic beam before proceeding with the subsequent shockwaves of the treatment. As a result, fewer lithotripsy treatments will reach completion without fragmenting the stone. Finally, as the method is used passively to monitor the reflections and emissions during treatment, there is no need for the additional interrogative radiation of the patient using ultrasound or X-ray fluoroscopy, which are used in the prior art methods to determine whether a stone has been fragmented. Neither the patient, nor the operator, will be exposed to unnecessary radiation.

Preferably, the assessment will further comprise the step of filtering the passive acoustic signal using either analogue or digital technology. This is because, for example, cavitation components present their main contribution at frequencies above 400 kHz and the filtering is required to extract the secondary acoustic emissions. Where the signal to noise ratio is less than about 50%, it may be desirable to filter the signal before digitisation. Most preferably, therefore, the signal is filtered via an analogue filter, before digitisation of the signal.

Preferably, the characteristics of the passive acoustic signal measured will be a first peak amplitude value ($m_1$), a second peak amplitude value ($m_2$) and a time interval value ($t_c$) between the first and second peak amplitude values, said values being indicative of the degree of degree of fragmentation and accuracy of targeting. During development of the present invention, a database of threshold values has been produced based on clinical use which accurately predicts the accuracy of focus and effectiveness of each shockwave, and whether a stone will be fragmented as a result of a treatment.

Preferably, a shockwave is classified as 'effective' if the ratio of the first and second peak amplitude values ($m_2$)/($m_1$) is between about 0.4 and about 0.8, and the time interval value ($t_c$) is greater than about 100 microseconds. Using clinical data described in this patent application, the inventors have developed an algorithm based on the selected signal characteristics that has been shown to successfully predict whether a shockwave is 'effective' or 'not effective'. In other words, the algorithm can be used to predict whether a generated shockwave would contribute to fragmentation of a stone or not.

According to another aspect, the classification method may be used to predict the outcome of an SWL treatment. The method would then include the further steps of repeating the classification method as hereinabove described for each shockwave in the treatment, determining the percentage of 'effective' shockwaves in the treatment to give a treatment score $TS_0$ and comparing the $TS_0$ with pre-set values to determine whether stone fragmentation has occurred. The treatment scope may also be reviewed by the practitioner at any stage in the treatment so that a 'real time' assessment of the treatment can be carried out.

Preferably, a $TS_0$ value of 50% indicates stone fragmentation. This value indicates that at least 50% of shocks in a treatment were effective, and has been shown to predict the outcome of a treatment (in terms of 'fragmentation' or 'no fragmentation') with greater accuracy than the currently used methods of post-lithotripsy X-ray fluoroscopy analysis.

According to another aspect of the present invention, there is provided a method of extracorporeal shockwave lithotripsy treatment, comprising positioning a passive unfocused acoustic sensor externally on a patient's torso, generating a shockwave directed towards a stone or stones, receiving an acoustic signal at the sensor following generation of the shockwave, determining whether at least one characteristic of the received acoustic signal exceeds a respective pre-determined threshold values and classifying the shockwave as effective or ineffective in dependence upon said determination.

This method of lithotripsy includes an automatic real-time monitoring capability. As such, the lithotripsy treatment will be monitored as it proceeds, to keep the operator informed of the progress and success, shock-by-shock, of the treatment.

Preferably, the lithotripsy treatment method will further comprise the step of filtering the received acoustic signal from the sensor, for example to extract the secondary acoustic emissions.

Preferably, the characteristics of the passive acoustic signal measured are a first peak amplitude value ($m_1$), time interval value ($t_c$) and a second peak amplitude value ($m_2$), said values being indicative of the degree of degree of fragmentation and accuracy of targeting. During development of the present invention, a database of threshold values has been produced based on clinical use which accurately predict the accuracy of focus and level of cavitation which is induced per shockwave, and whether a stone will be fragmented as a result of a treatment.

Preferably, the method involves processing a signal representative of a detected passive acoustic signal and classifying a shockwave as 'effective' if the signal shows a ratio of $0.40 < (m_2)/(m_1) < 0.8$ and a ($t_c$) value of >100 microseconds. Using clinical data described in this patent application, the inventors have developed an algorithm based on the selected signal characteristics which has been shown to successfully predict whether a shockwave is 'effect' or 'not effective'. In other words, to predict whether it would contribute to fragmentation of a stone or not.

Preferably, the method of lithotripsy treatment will further comprise adjusting the focal point of the shockwave before generating a subsequent shockwave if the first peak amplitude values ($m_1$) of a sufficient number of shockwaves do not exceed a pre-set threshold value. Current results suggest that 300-500 such shocks would be sufficient to show that adjustment is required. By continually monitoring and adjusting the focal point of the beam, the operator can ensure that more shock are 'on-target', i.e. that the focal point of the beam is appropriately coincident with the position of the stone. The ability to adjust the treatment and improve its effectiveness in real-time will allow the operator to improve re-treatment rates. Currently, re-treatment rates are high, at approximately 30-50%, and patients can sometimes require up to 6 treatments before a stone is fragmented. Reducing the re-treatment rate using this method of improved lithotripsy treatment will in turn reduce costs for the operator or health trust and also reduce collateral damage to the patient.

Preferably, the method of lithotripsy treatment will further comprise increasing the energy level of the shockwave to improve fragmentation before continuing with the treatment if the time interval value ($t_c$) is greater than 100 microseconds, indicating that the shockwave is on target, but the value of $m_2/m_1$ for a sufficient proportion of a test dose of shockwaves does not exceed a pre-set threshold amplitude value. Current results suggest that a test dose of 300-500 shocks would be sufficient to show that adjustment is required. Preferably, the method of lithotripsy treatment will further comprise decreasing the energy level of the shockwave to reduce collateral damage before proceeding with a further shockwave if the time interval value ($t_c$) and a second peak amplitude value ($m_2$) for a sufficient proportion of a test dose of shockwaves does not exceed a pre-set threshold amplitude value. Current results suggest that a test dose of 300-500 shocks would be sufficient to show that adjustment is required.

Preferably, the method of lithotripsy will further comprise producing a figure TS(t) representing cumulative effectiveness of shockwaves during the treatment. This figure will indicate the percentage number of shocks that have, up to the point at which the operator notes the figure TS(t), been effective. If, once a statistically significant number of passive acoustic emissions have been recorded during a treatment, the operator can see that the value of this figure is not high enough, he can re-focus or otherwise adjust the acoustic beam to improve the likelihood of a successful lithotripsy treatment.

Preferably, the method of lithotripsy will further comprise continually monitoring the TS(t) and reducing the number of shockwaves in a treatment if the TS(t) indicates that further shockwaves are unnecessary for fragmentation. The operator can thus take a view on the treatment outcome, and decide whether it is possible to subject the patient to fewer shockwaves. This will reduce the level of collateral damage that will be suffered by the patient unnecessarily.

Preferably, the depth of respiration is monitored from the measured characteristics of the acoustic signal to provide a respiratory gating signal for shockwave release.

According to another aspect of the present invention, there is provided an assessment system for a lithotripsy treatment comprising a clinical passive unfocused acoustic sensor, a high pass filter, an oscilloscope, and a computer configured with software to process the filtered signals from the sensor to determine if the treatment is successful. This system conveniently allows full assessment of the lithotripsy treatment, including acoustic detection, signal conversion, signal filtering and analysis of the various components of the signal.

According to aspects of the present invention, there is provided a clinical passive unfocused acoustic sensor for detection of acoustic emissions according to the method and system as hereinabove described.

In an embodiment, the sensor comprises a protective front face, a piezoelectric active element, a backing material and a connector all enclosed in a round smooth disc shaped first housing and a wideband preamplifier wherein the disc shaped housing and the wideband preamplifier are located within a second housing unit. The shape of the first housing is configured to be comfortable to the patient and also for maximum signal to noise ratio. The preamplifier is placed in the second housing and connected to the output of the passive unfocused acoustic sensor via the connection, to overcome a problem of poor signal to noise ratio. This was experienced particularly for patients with body mass indices of more than 25.

Preferably, the piezoelectric layer active element includes a biocompatible acoustically-sensitive front face. This ensures that the patient is protected from the electrical components of the system whilst allowing the front face to be disinfected easily with solvents such as isopropyl alcohol before applying the passive unfocused acoustic sensor to a patient. This reduces the risk of spreading infection between patients.

Preferably, the wideband preamplifier buffers the electrical impedance to 50 Ohms. This buffer level ensures that the signal to noise ratio is maximal even where the patient has a BMI of more than 25.

Preferably, the passive unfocused acoustic sensor has a sensitivity of 3.3 V/MPa at 500 kHz, and the combination of the sensor and the preamplifier have a sensitivity of between 20-22 V/MPa at 500 kHz. Most preferably, the combination of the preamplifier and the sensor has a sensitivity of 20 V/MPa at 500 kHz. This sensitivity is necessary to achieve a detectable signal, in particular because the secondary acoustic emissions contain useful energy at a frequency component of around 400 kHz. At higher sensitivities, saturation of the preamplifier was observed to occur.

BRIEF DESCRIPTION OF THE DRAWINGS

Specific embodiments of the present invention will now be described with reference to the accompanying drawings, in which:

FIG. 7a is a graph showing a raw signal collected in vivo with the passive unfocused acoustic sensor;

FIG. 7b is a graph showing a signal collected in vivo with the passive acoustic unfocused sensor and then filtered by a high Pass Butterworth filter;

FIG. 9b is a graph showing the power distribution function I(t) corresponding to the signal in FIG. 9a;

FIG. 10 is a diagram showing the parameter $m_2/m_1$ for emissions collected in vitro adjacent to stone phantoms at different grades of fragmentation;

DETAILED DESCRIPTION OF EMBODIMENTS OF THE INVENTION

System Overview

Figure 1:
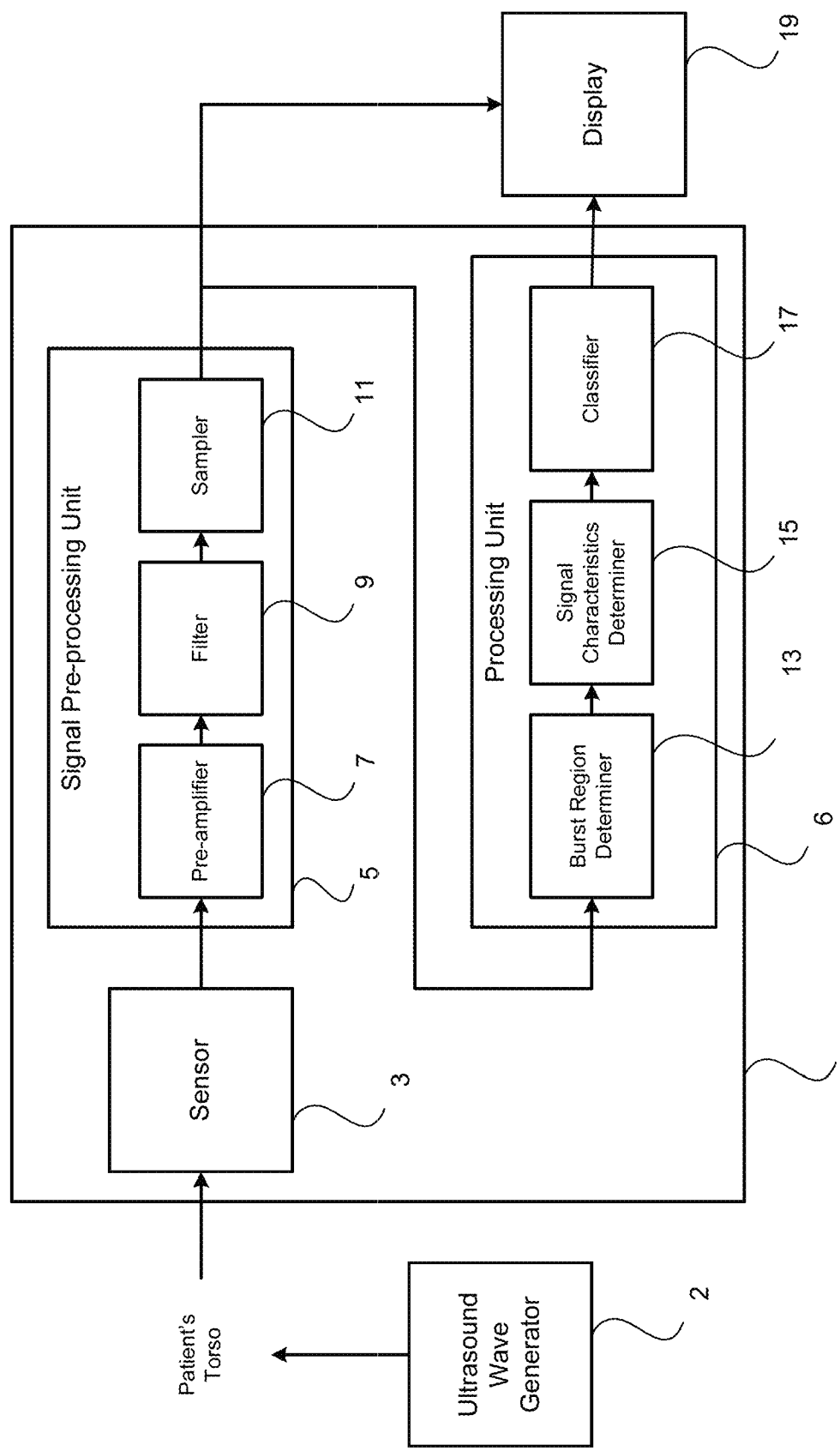
FIG. 1 is a block diagram of the ultrasound diagnostic system according to an embodiment of the present invention.

The system according to the invention is designed to detect acoustic emissions and reflections from an area treated with SWL, in order to determine the efficacy of a treatment. FIG. 1 is a block diagram illustrating the functional components of the system 1 designed to acquire and process the acoustic signal according to the present embodiment. As shown in FIG. 1, an ultrasound shockwave generator 2 generates an ultrasound shockwave which is directed to an area of a patient's torso to be treated. The system 1 includes an ultrasound passive unfocused acoustic sensor 3 for receiving an acoustic signal following generation of the shockwave, a signal pre-processing unit 5 for receiving and performing pre-processing of the received acoustic signal, and a signal processing unit 6 for receiving and processing the pre-processed acoustic signal to classify the shockwave as effective or ineffective, as will be described in detail below. In this embodiment, the signal pre-processing unit 5 includes a pre-amplifier 7, a filter 9 and a sampler 11, which may be an oscilloscope for example. As those skilled in the art will appreciate, the signal pre-processing unit 5 may comprise circuitry within a single unit or several separate units.

The signal processing unit 6 includes a signal characteristics determiner 15 and a classifier 17 for processing the signal. As will be described in more detail below, the signal characteristics determiner 15 determines the characteristics of the pre-processed acoustic signal, which in this embodiment are a first peak amplitude value ($m_1$), a second peak amplitude value ($m_2$) and a time interval value ($t_c$) between the first and second peak amplitude values, the characteristics values being indicative of the degree of degree of fragmentation and accuracy of targeting. The classifier 17 then classifies the shockwave as 'effective' or 'ineffective' based on the determined characteristics as discussed below.

Figure 2:
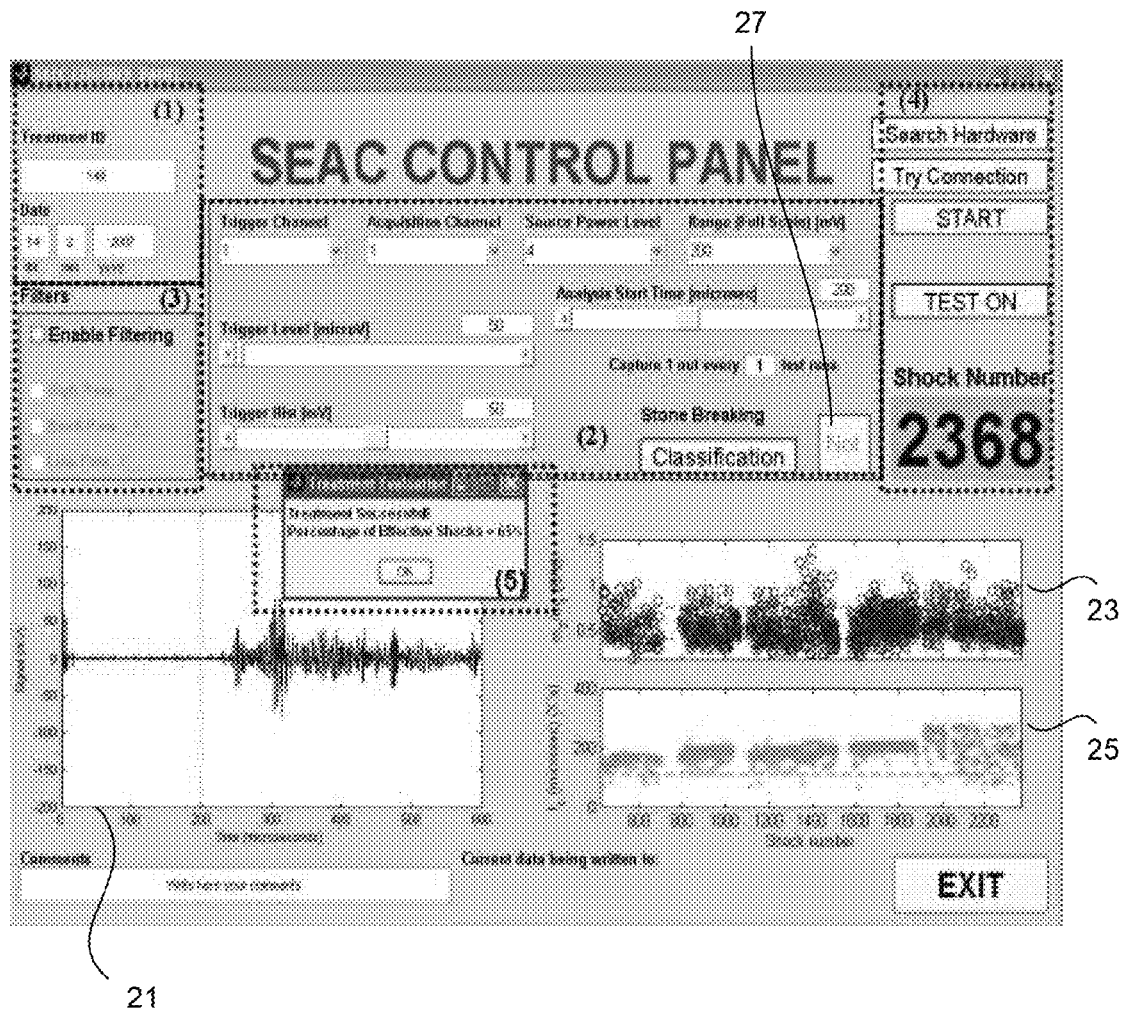
FIG. 2 is a screen shot of the user interface, or control panel, of the SEAC/MATLAB software.

The user can view the results of the processing on a display 19, such as a monitor for displaying a SEAC/MATLAB interface. FIG. 2 illustrates an example of such a display, showing a representation of the received acoustic signal in a first window 21, a representation of the values of a first signal characteristic value ($m_2/m_1$) in a second window 23, and a representation of a second signal characteristic value ($t_c$) in a third window 25, and subsequently the outcome of the classification 27 of each generated shockwave as effective or not, and the outcome of the classification process ($TS_t$) as a whole which will be displayed in real time in a pop up window 27.

The system is described in greater detail in "A passive acoustic device for real-time monitoring the efficacy of shockwave lithotripsy treatment", Leighton et al., *Ultrasound in Medicine and Biology*, 34(10), 2008:1651-1665, the contents of which are herein incorporated by reference in their entirety.

Ultrasound Passive Unfocused Sensor

Figure 3A:
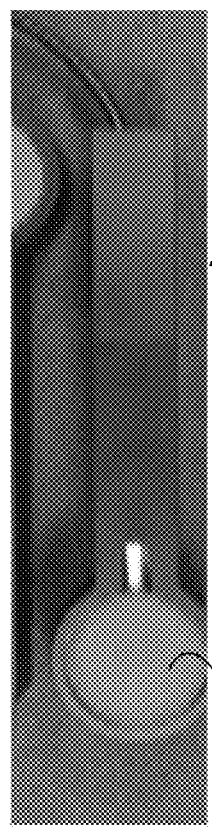
FIGS. 3a and 3b are photographs of the passive unfocused acoustic sensor.
Figure 3B:
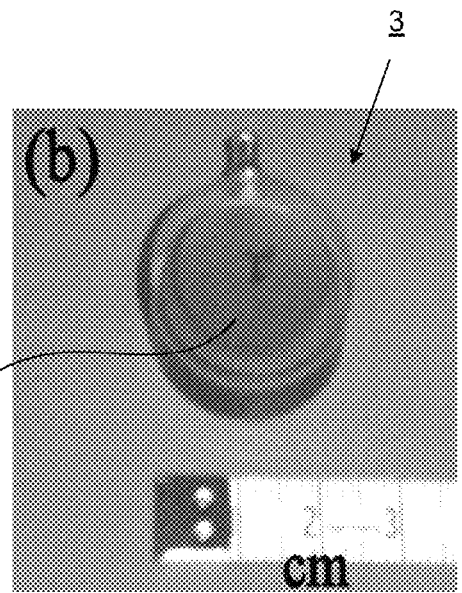
Figure 5:
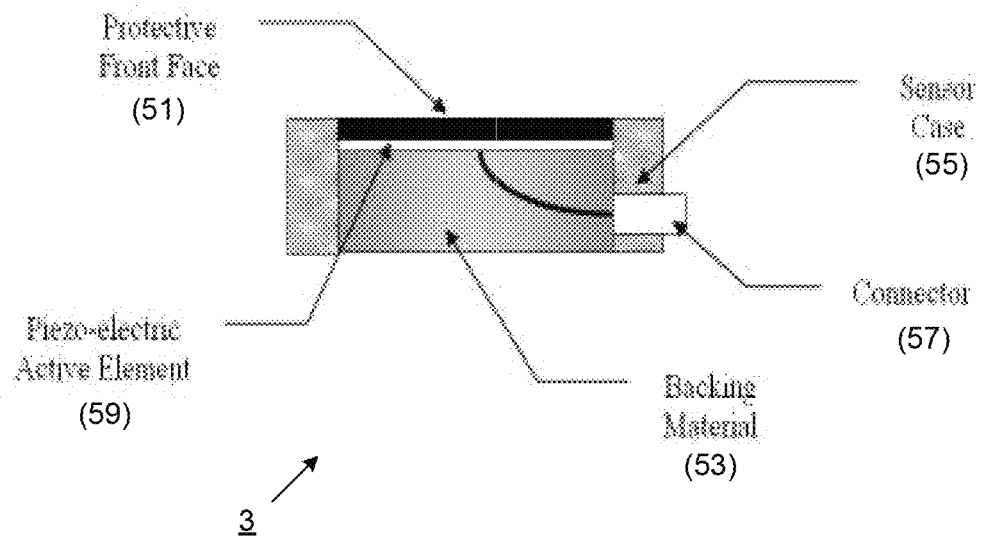
FIG. 5 is a diagram of the passive unfocused acoustic sensor.

FIG. 3a shows an example of an ultrasound passive unfocused acoustic sensor 3 according to an embodiment of the present invention. In this embodiment, the sensor 3 is attached externally on a patient's torso and positioned as close as possible to the treated area. Three different passive prototypes were initially developed. For both technical and aesthetical reasons, a round smooth single channel sensor was developed that could make the patient feel comfortable. In an embodiment, the 'Mark III' passive unfocused acoustic sensor 3 shown in FIG. 3a is an entirely passive piezoelectric sensor with a diameter of 25 mm that converts received pressure waves into measurable voltages. FIG. 5 shows the structure of the sensor 3. The sensitive element 59 is a thin (28 μm) Polyvinylidene Flouride (PVdF) film of 18 mm diameter with a broadband frequency response up to 100 MHz. It should be noted that in general, the frequency response is only required to be up to 2 MHz.

Figure 4:
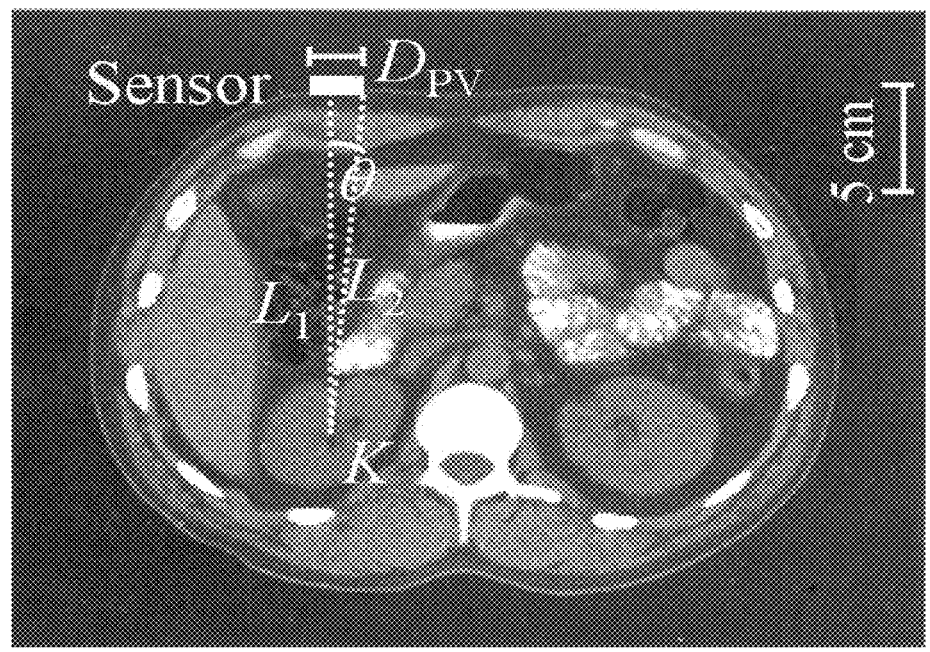
FIG. 4 is a computer tomographic image of a human torso indicating acoustic path lengths.

The diameter of this sensitive film element 59 was designed to ensure that at 3 MHz, a maximum path difference $L_M = L_2 - L_1$ (see FIG. 4) no greater than 0.25 mm (which is equivalent to $0.5 \times \lambda_{3M}$, with $\lambda_{3M}$=500 μm sound wavelength at 3 MHz) would occur for emissions coming from the kidney. That is to say, FIG. 4 shows two possible emissions paths coming from the kidney K, each path having a respective length $L_1$ and $L_2$. A frequency of 3 MHz was used, as this is the maximum frequency expected to reach the surface of the torso from the kidney (depths of about 17 cm) because of ultrasound attenuation by the body.

If there is a maximum path difference ($L_M$), equal to half the diameter of the PVdF film element $L_M$=1 mm, then the maximum allowable diameter $D_{PV}$ can be derived from geometrical considerations as:

$$L_2 - L_1 = L_2(1 - \cos\theta) < 0.5\lambda_{3\,M} \quad (1)$$

$$\frac{D_{PV}}{2} = L_2 \sin\theta \quad (2)$$

where θ is the angle between the two paths $L_1$, $L_2$. The combination and manipulation of these two conditions (1) and (2) leads to:

$$D_{PV} < \sqrt{4L_2^2\left[1 - \left(1 - \frac{0.5\lambda_{3\,M}}{L_2}\right)^2\right]} = 26 \text{ mm} \quad (3)$$

as $L_2$ has been estimated to be about 17 cm for the average patient. This information was gathered from anatomical data available as cross sectional images of the human body and records of the distances of kidney stones from the patient torso reported in a database of sixty patients that had undergone the SWL at Guy's Hospital between 1998 and 2000.

As shown in FIG. 5, the front face of the piezo-electric sensor 31, which is in contact with the patient, is protected by a protective front face 51, which in this embodiment is formed of an insulating bio-compatible material whose acoustic properties were optimized to ensure the maximum acoustic sensitivity of the system. The insulation is necessary to comply with the requirements of electrical safety normative (IEC60601-1), which are imposed to avoid that a patient becomes part of any electrical path that connects to the mains power supply. The protective front face 51 can also be disinfected easily with solvents such as Isopropyl Alcohol before applying the passive unfocused sensor to a patient. This is to prevent possible spread of infections among patients. In contrast, the rear surface 53 of the passive unfocused sensor 3 is filled with a sound absorbing material, for example Aptflex as developed by the National Physics Laboratory (NPL) that prevents internal reverberations within the sensor 3.

Furthermore all elements of the passive unfocused acoustic sensor 3 are placed in an electrically conducting grounded enclosure, which is connected to both the ground electrode on the sensitive element 31 and the signal ground of a connector 57 on the enclosure wall. The voltage waveform generated within the piezoelectric element is extracted by means of the wide bandwidth RF connector 57 mounted in the side wall of the passive unfocused sensor case 55. All components of the acoustic sensor 3, with the exception of the connector 57 and the wires attached to it, are polymeric. This results in a lightweight passive unfocused sensor 3 (total weight for example 7 g) to minimize patient discomfort. In the present embodiment, the sensor 3 has a sensitivity of 3.3 VMPa$^{-1}$ at 500 kHz.

In this way, the sensor 3 of the present embodiment is advantageous because it is passive so no additional ultrasound dose is given to patient and it is unfocused which allows the sensor 3 to be less bulky than known focused sensors which places less restrictions on positioning and alignment of the sensor 3.

Signal Pre-Processing Unit

The pre-amplifier 7 provided in the signal pre-processing unit 5 according to the present embodiment will now be described. The final prototype (Mark III), described in the previous subsection, did not always present signals of good quality when tested in vivo. That is to say that the signal to noise ratio, estimated as the ratio between the maximum amplitude of the first burst $m_1$ and the background noise level was greater than 50% only for patients underweight or of regular corporature, i.e. patients with body mass indices (BMI) less than 25. In order to overcome this problem, the output of the passive unfocused acoustic sensor 3 was connected directly to a wideband pre-amplifier 7 (such as pre-amplifier model HP1, by Precision Acoustics Ltd, Dorchester, UK) that buffered the electrical impedance to 50 Ohms. In this embodiment, the commercially available preamplifier required a DC Supply voltage of 28±1 V (to ensure a variation in the system gain <1%) and was for this reason connected to a DC coupler. The pre-amplifier 7 is also consistent with the design principles of a lightweight system (total weight of preamplifier/cable is 29 g). Patient safety (as mentioned in the previous subsection) required that, unless an insulating transformer or optical coupling was used, the sensor 3 applied to the patient could not be connected to the mains power supply. Therefore a battery powered DC supply may be used, for example by coupling four 9 V batteries via a DC coupler (not shown) to power the pre-amplifier.

Figure 6:
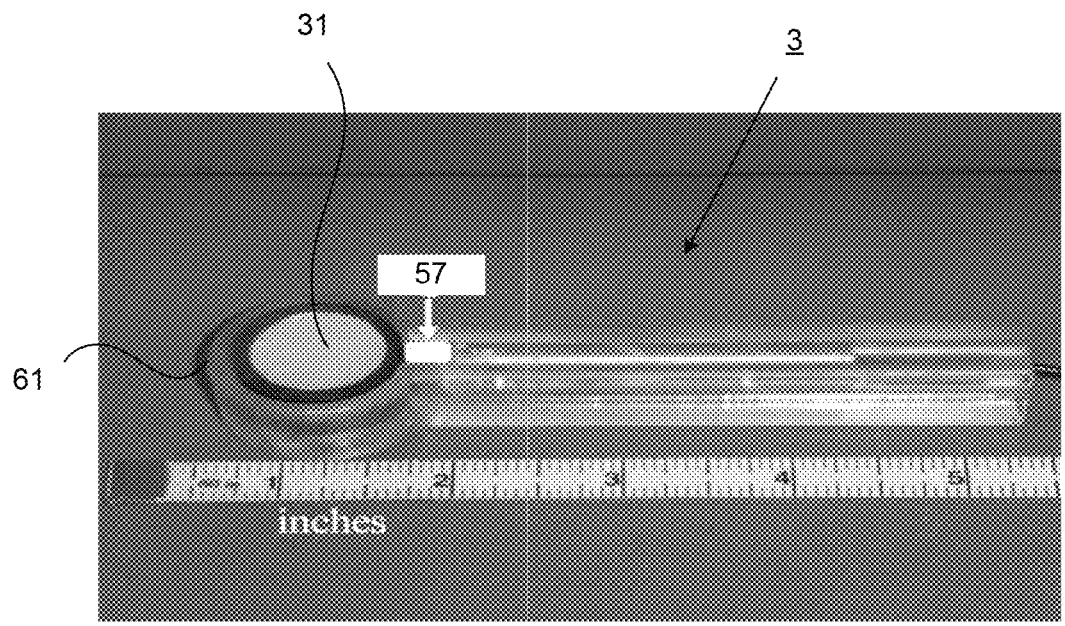
FIG. 6 is a photograph of the passive unfocused acoustic sensor and the preamplifier within the holder.

In this embodiment, the combination of the passive unfocused acoustic sensor 3 with the pre-amplifier 7 has a sensitivity of between 20-22 V/MPa, and preferably 21 V/MPa, when calibrated at 500 kHz. As shown in FIG. 6, the passive unfocused acoustic sensor 3 and pre-amplifier 7 are encapsulated in a rigid polymethyl methacrylate (PMMA) holder 61 that protects the components. In particular, the use of this holder 61 avoids the possibility that any stress could be applied to the contact between the passive unfocused acoustic sensor 3 and the pre-amplifier 7. This holder ensures, at the same time, the insulation of any possible electrical contact from the patient. The total weight of the part applied to the patient (sensor 3, pre-amplifier 7 and PMMA holder 61) in this embodiment is about 52 g and is therefore still such as not to induce any discomfort to the patient.

The filter 9 in the system according to the present embodiment shown in FIG. 1 will now be described. In this embodiment, the background noise and the lithotripter shock are filtered to extract the secondary acoustic emissions. This is because the cavitation components presented their main contribution at frequencies above 400 kHz. FIG. 7a shows a raw signal collected by means of the clinical passive unfocused acoustic sensor 3 in vivo. FIG. 7b shows the same signal after it has been filtered by means of digital high pass filter. For example, the filter used may be a Butterworth filter of $4^{th}$ order with a cut-off frequency at 3 dB of 300 kHz and a reduction of about 128 dB at 120 kHz. The digital filtering may be applied twice (forward and backward), for example to compensate for any phase shift introduced by the filter.

As mentioned above, digital filtering is an option for signals with a signal to noise ratio of at least 50%. In all the other cases, it was desirable to filter the signal before digitisation. As an alternative, the filter 9 may include a high pass filter with characteristics as close as possible to that of the Butterworth filter discussed above. The high pass filter may have a cut-off frequency $f_c$ at 3 dB of 292 kHz and show an attenuation of about 120 dB at 120 kHz. The phase spectrum of this high pass filter is linear in the main region of interest (0.3-1 MHz). This ensures that any delay introduced by the filter was constant for the different frequency components of the signal and did not alter the signal characteristics. It is possible for the system to include low pass, band-pass and/or high pass filters or a combination of these to extract some specific frequency components. This would, for example, assist the isolation of some phenomena. Scattering components, for example are expected at lower frequencies (<400 kHz) rather than cavitation components which are expected at higher frequencies (>400 kHz). Therefore, low pass filtering might be expected to enhance the scattering component. On the other hand, high pass filtering as explained above would enhance the cavitation component. As another example, Band-pass filtering could be used to enhance cavitation and eliminate, at the same time, eventual high frequency interference/noise above the maximum frequency of interest (about 1 MHz).

As shown in FIG. 1, the filtered signal is passed from the filter 9 to a sampler 11 which in this embodiment is a TiePie digital oscilloscope, chosen from among other available A/D modules essentially for its portability and the ability to operate without an external power supply. The latter feature ensured that the system could easily satisfy the electrical requirements of medical devices of class BF (according to the classification of the International Electrotechnical Commission), i.e. devices with floating parts applied to a patient (IEC60601-1), because it was powered such that it could operate using its own battery (20V). However, those skilled in the art will appreciate that as an alternative, the whole system 1 of data acquisition may instead be configured to be powered via the mains power supply in a manner which is safe for the patient during prolonged acquisition sessions. In this alternative, any background noise present in the acquired signals may be eliminated before any data processing by means of digital filtering.

As those skilled in the art will appreciate, as an alternative, it is not necessary to pre-process the signal from the sensor 3 using dedicated pre-processing circuitry, for example if the sensor was adapted to provide a signal suitable for direct processing by the processing unit described below.

Processing Unit

As shown in FIG. 1, the system 1 includes a processing unit 6, which in this embodiment is a programmable device, such as a computer, programmed with a MATLAB program to provide a signal characteristic determiner 13 which determines the values of characteristics of the signal received from the pre-processing unit 5. As discussed above, in the present embodiment, the characteristics are a first peak amplitude value $m_1$ of a first detected burst region of the signal, a second peak amplitude $m_2$ of a second detected burst region, and a time, $t_c$, between the first burst region and the second burst region. As will be described in detail below, this time value can be estimated in several ways. Preferably the time value $t_c$ is calculated as the interval between the two burst region central times. However, as an alternative, the time between the two peaks $m_1$ or $m_2$ could be used as an estimate. The processing unit 6 also includes a shockwave classifier which compares these values with predetermined threshold values, and classifies the shockwave as 'effective' or 'ineffective' depending on the determination as to whether each characteristic meets a respective predetermined threshold value.

Figure 8:
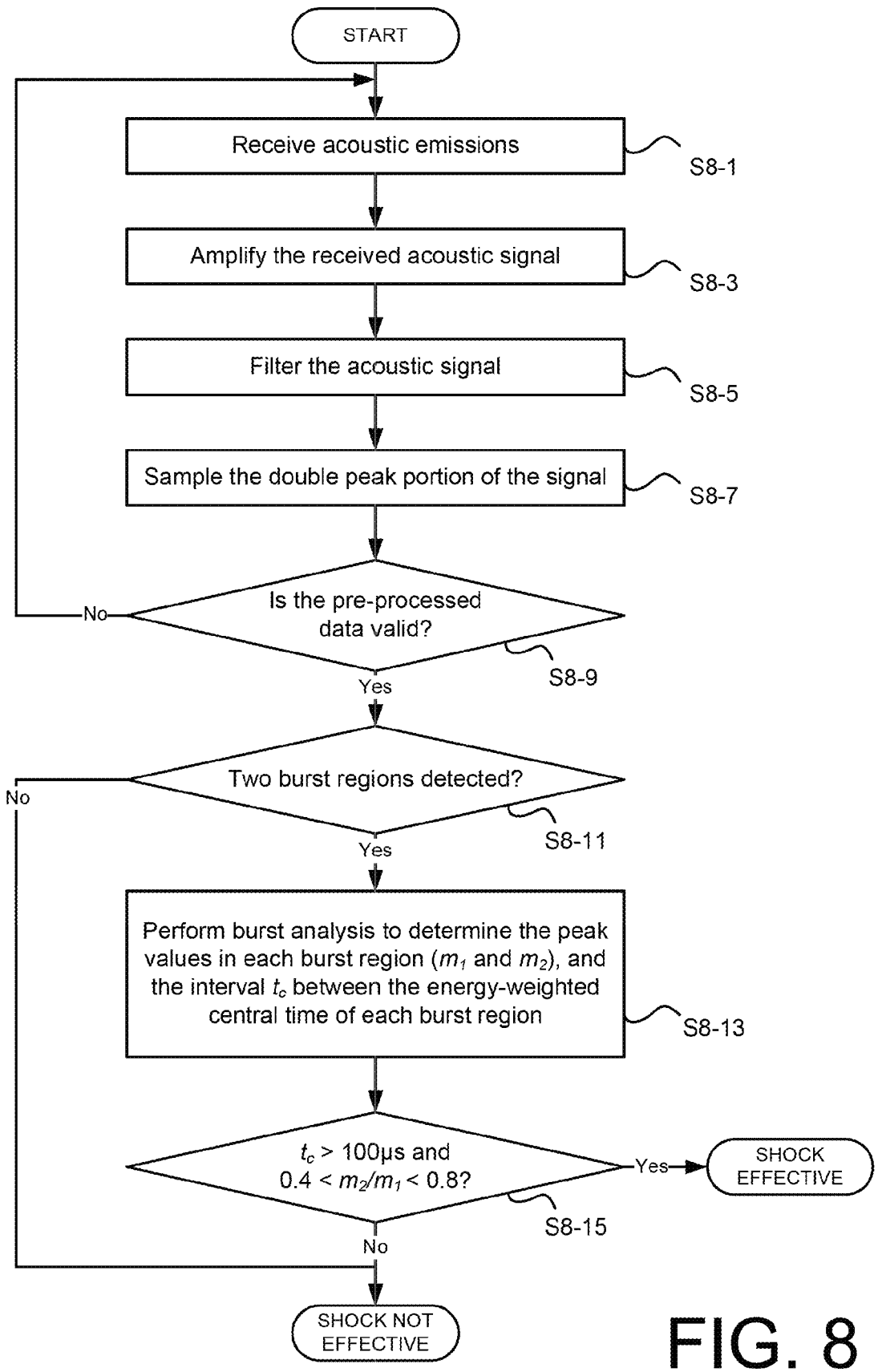
FIG. 8 is a flow diagram illustrating the processing steps performed by the system of FIG. 1 to classify a shockwave according to an embodiment of the present invention.

The processing performed by the components of the processing unit will now be described in more detail with reference to FIG. 8. FIG. 8 is a flow diagram illustrating the steps of the optimised method of analysing the acoustic emissions. The passive unfocused acoustic sensor 3 is placed against the torso of the patient, as close as possible to the treated area. At step S8-1, the sensor 3 receives the acoustic emissions that result from the SWL treatment. At step S8-3, the acoustic signal is amplified by the pre-amplifier 7 and then filtered at step S8-5 by the filter 9 to extract the secondary emissions. The filtration can alternatively be performed on a digitised signal, but where the signal to noise ratio is less than 50%, it is preferable to filter the acoustic signal. The amplified and filtered signal is then fed into the sampler 11, such as an oscilloscope, which samples at step S8-7 the appropriate portion of the signal, which is the 'double peak' portion as described below. The amplified, filtered and sampled signal is then fed into the processing unit 6.

At step S8-9, the processing unit 6 processes the received signal data to determine whether the data is valid. As those skilled in the art will appreciate, the data may be erroneous if the system was false triggered and therefore the processing unit 6 may be arranged to look for null data or an empty matrix indicative of invalid data. If the data is not valid, processing returns to step S8-1 where the sensor 3 receives a new acoustic emission. On the other hand, if the data is valid, then at step S8-11, the burst region determiner 13 in the processing unit 6 processes the pre-processed signal received from the signal pre-processor 5 to determine whether a first burst region and a second burst region can be detected in the received signal.

Figure 9A:
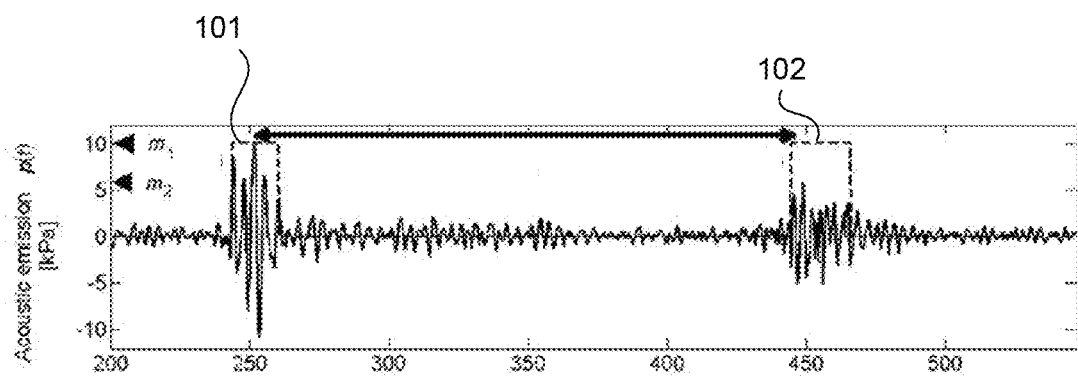
FIG. 9a is a graph showing a signal collected in vivo with the passive acoustic unfocused sensor and then filtered and preamplified by analogue devices.
Figure 9B:
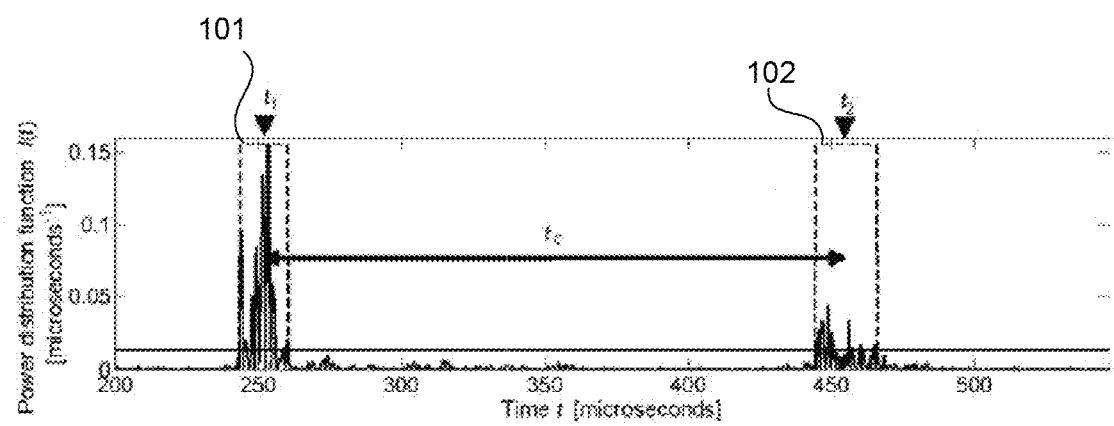

The detection of the burst regions 101, 102 involves an initial calculation of a power function I(t) from the voltage waveform p(t) of the received signal:

$$I(t) = \frac{p^2(t)}{\int_{t_i}^{t_i+\tau} p^2(t') dt'} \quad (4)$$

where the integral is calculated over a time τ long enough to contain the whole signal (τ=400 μS). A plot of I(t) is shown in FIG. 9b. In this quadratic signal, the two burst regions 101 and 102 (which are those portions of the signal at highest powers $p^2(t)$) are emphasized above the noise level. In addition, the signal I(t) is defined to have a unitary integral over the interval considered, so that it represents a distribution function of the power in that interval. In this embodiment, the threshold is taken at the 96th percentile of I(t) although the invention is not limited in this regard. The algorithm identifies the two burst regions 101 and 102 (as illustrated in FIGS. 9a and 9b) as the two regions of adjacent points that are above the threshold. FIG. 9a is a graph showing the two portions of the signal recognised as the first burst region 101 and the second burst region 102. The two signal characteristics $m_1$ and $m_2$ are also indicated. FIG. 9b is a graph showing the power distribution function I(t) corresponding to the signal in FIG. 9a. The graph also shows the estimated central times of the two bursts, $t_1$ and $t_2$, and the interval $t_c$.

A minimum separation time of 20 microseconds is imposed between the two regions 101,102, except for the special circumstance when the signal is such that a second burst region cannot be detected above the noise, whereupon the algorithm allocates a conventional value of $t_c$=0 and $m_2$=0 to the signal. In such a case, the processing unit 6 indicates an "ineffective" targeting for the generated shockwave, although, as those skilled in the art will appreciate, some such signals may originate from equipment-related effects such as poor acoustic coupling between the sensor 3 and the skin. Therefore, if it is determined at step S8-11 that a second burst region cannot be detected, then the processing unit 6 determines that the shockwave is not effective and the processing for that shockwave terminates.

On the other hand, if it is determined at step S8-11 that two burst regions are detected, then at step S8-13, the signal characteristic determiner 15 determines acoustic parameters associated with each burst. Once the burst regions 101 and 102 have been identified, the peak values ($m_1$ and $m_2$) in each burst region 101 and 102 are determined, for example by looking for the maximum amplitude within the respective burst region. In addition, a single energy-weighted central time $t_1$ is allocated to each of the two regions 101 and 102 using:

$$t_i = \int_{t_{i,min}}^{t_{i,max}} t I_i(t) dt \quad (5)$$

where i=1, 2 indicates which burst is under consideration, and where $I_i(t)$ is the relative power distribution function of the ith region. That is to say, $I_i(t)$ is calculated using equation (5) but with the integration of the denominator occurring from $t_{i,min}$ (the start time of the burst under consideration) to $t_{i,max}$ (the end time of the burst under consideration). Having calculated $t_1$ and $t_2$ in this way, the interval $t_c$ is found from $t_c=t_2-t_1$. These parameters are shown in FIG. 9b. This estimate, $t_c$, is advantageous because it is robust and less dependent on noise; but as mentioned above, the time interval value $t_c$ could simply be calculated from the time between the maximum values of each burst region.

Once the acoustic characteristics have been determined by the signal characteristics determiner 15, then at step S8-15, the shockwave classifier 17 in the processing unit 6 compares the values of $m_2/m_1$ and $t_c$ with the threshold values known to be associated with effective shockwaves to classify the shockwave as 'effective' or 'ineffective' depending on whether the determined values exceed the threshold values (effective) or do not meet the threshold values (ineffective). As will be discussed below, an effective shockwave may be determined as one for which a ratio of $(m_2)/(m_1)$ between about 0.4 and about 0.8 and a time interval value $(t_c)$ greater than about 100 microseconds is measured. As those skilled in the art will appreciate, if the threshold value is inverted, the classifier 17 may be arranged to determine that the shockwave is effective if the threshold values are not exceeded.

As mentioned above, a single SWL treatment may involve as many as 3000 generated shockwaves directed at the treatment area, the actual number of shockwaves depending for example on the patient's health and tolerance. As the SWL treatment progresses, the processing unit 6 in the present embodiment is arranged to receive and process passive acoustic signals from the sensor 3 representative of a subset of the generated shockwaves for that particular treatment cycle, as sampled by the sampler 11 discussed above. In this way, the processing unit 6 therefore classifies a sampled subset of the generated shockwaves as effective or ineffective and produces a treatment score TS(t) which provides a real-time assessment of the success of the treatment based on the percentage of 'effective' shockwaves. An overall score $TS_0$ is thus calculated by the processing unit 6 at the end of the treatment cycle, and a treatment outcome can be determined by the processing unit 6. In this embodiment, the processing unit 6 determines that the treatment is successful if more than 49.4% of the sampled shockwaves are classified as effective. Of course, those skilled in the art will appreciate that the present invention is not limited to this precise threshold which was determined from a statistical analysis of test acoustic data when compared with subsequent x-ray assessment, as discussed in greater detail below.

The detailed process and theory underlying the development of various aspects of the system and the method of using it will now be discussed.

Preliminary Development of the Sensor and the Pre-Processing Unit

The system was preliminarily tested in vitro to determine whether the system could be used to capture the acoustic reflections and emissions associated with SWL. First of all, the signal received from the sensor was read at the output of the pre-processing unit of an embodiment of the present system (without the use of a pre-amplifier) and compared with the signal acquired exploiting a known NPL cavitation sensor. The known NPL cavitation sensor was left at the focus of bench-top lithotripter, while the passive unfocused acoustic sensor 3 of the present invention was placed laterally off-axis at different distances varying from 0.5 to 30 mm.

Two traces were recorded while testing the prototype at the minimum distance of 0.5 mm. The traces were then analyzed to determine to what extent the time history can be interpreted as a double-peak feature consisting of a first peak $m_1$, and second peak $m_2$, and the time elapsing between $m_1$ and $m_2$, known as $t_c$. This 'double peak' feature of the trace results from a combination of the interactions between the SWL incident shock wave and the body, including scattering of that shock wave from the stone, cavitation, and the development of pressure fields within and outside of the stone. The detailed theoretical understanding of some of the key features will be described herein below. This double-peak feature is not always obvious from visual inspection of the time history, but can be revealed by processing. Some correlation (square of the maximum correlation coefficient $r_c^2$ equal to 0.4) was found in vitro between the signals from the known NPL sensor (which could not be used in vivo) and the Mark III sensor of the present invention and, most importantly, they did not show significantly different features. This is to say, the average value of $t_c$ (representing the accuracy of targeting of the stone with the shockwave) and the average index calculated from $m_2/m_1$ (representing levels of cavitation/fragmentation) of sets of 5 traces collected using the two systems were compared using t-test statistics. Neither of the set of values (from the NPL sensor or the sensor of the embodiment described above) showed any statistical difference when tested for a significance (p-value) less than 0.01. In particular, the values estimated for the time $t_c$ were 240±5 µs for the NPL sensor and 226±14 µs for the clinical passive unfocused acoustic sensor. The values estimated for the fragmentation index $m_2/m_1$ were 0.52±0.06 for the NPL sensor and 0.43±0.05 for the clinical sensor. The correlation between the signals decreased when the clinical prototype sensor according to the invention was moved further away from the focal point. Traces collected at a distance d equal to 30 mm showed a square cross correlation coefficient equal to 0.15.

Following these experiments the clinical prototype was tested in vitro now in the proximity of stone phantoms, which had different pre-determined grades of fragmentation (as illustrated in FIG. 10). FIG. 10 is a diagram showing the parameter $m_2/m_1$ for emissions collected in vitro adjacent to stone phantoms at different grades of fragmentation, F. The results labelled (a) represent the emissions collected using the unfocused passive acoustic sensor 3 and where the stone phantoms are placed in a body phantom at the focus of a clinical lithotripter. The results labelled (b) represent the emissions which were recorded using the NPL sensor and where the stone phantoms are placed at the focus of bench-top research lithotripter. From the results of the experiments, the inventors observed a similar behaviour to that which had been found when using the known NPL sensor in the bench-top lithotripter. That is to say, the relative amplitude of the second burst ($m_2/m_1$) increased with the fragmentation ratio (FIG. 10, results labelled (a)) and, in particular, showed values higher than $m_2/m_1$–0.4 for a stone whose fragmentation was higher than 50%. These preliminary in vitro tests showed that the clinical prototype, when used in the clinical environment, could be used to gather information about targeting ($t_c$) and fragmentation ($m_2/m_1$) as discussed below.

A Guideline Explanation of the Signal Characteristics

An explanation of the understood mechanisms behind the observed 'double peak' structure will now be provided. It must be recognized that this description is provided as a guideline only to assist with the physical understanding of the two-peak structure and should not be taken as comprehensively encompassing all the relevant physics and biology. As discussed above, graphs of a sample pressure waveform obtained from the sensor 3 are provided in FIGS. 9a and 9b, showing the two detected burst regions 101 and 102 and a graphical model of cavitation behaviour in FIG. 11. The pressure waveform generated during clinical SWL is detected using a passive unfocused acoustic sensor placed on the skin, as close as possible to the treated area. The first 'burst', or first peak amplitude $m_1$, is a pressure pulse that includes emissions due to reflection from the stone and also, to a lesser extent, cavitation activity. Emissions due to cavitation activity tend to have a higher frequency than those due to the reflection of the shockwave, and therefore it is possible to determine the proportion of $m_1$ that relates to the former or the latter of these two options. The pressure profile acquired is complicated by the interaction of the pressure field in the tissue, any cavitation that is occurring and the pressure field within the stone. The second burst, or second peak amplitude $m_2$, may be a pressure pulse due to the interaction between the stone and the bubble cloud, when the cavitating bubbles collapse following a period of expansion. After the shockwaves have initially hit the bubble cloud and the intense reflections have caused $m_1$, the bubbles then undergo a period of expansion within a region of very high peak negative pressures in the acoustic field. The time $t_c$ represents the period of time for which the bubbles continue to expand.

Figure 11:
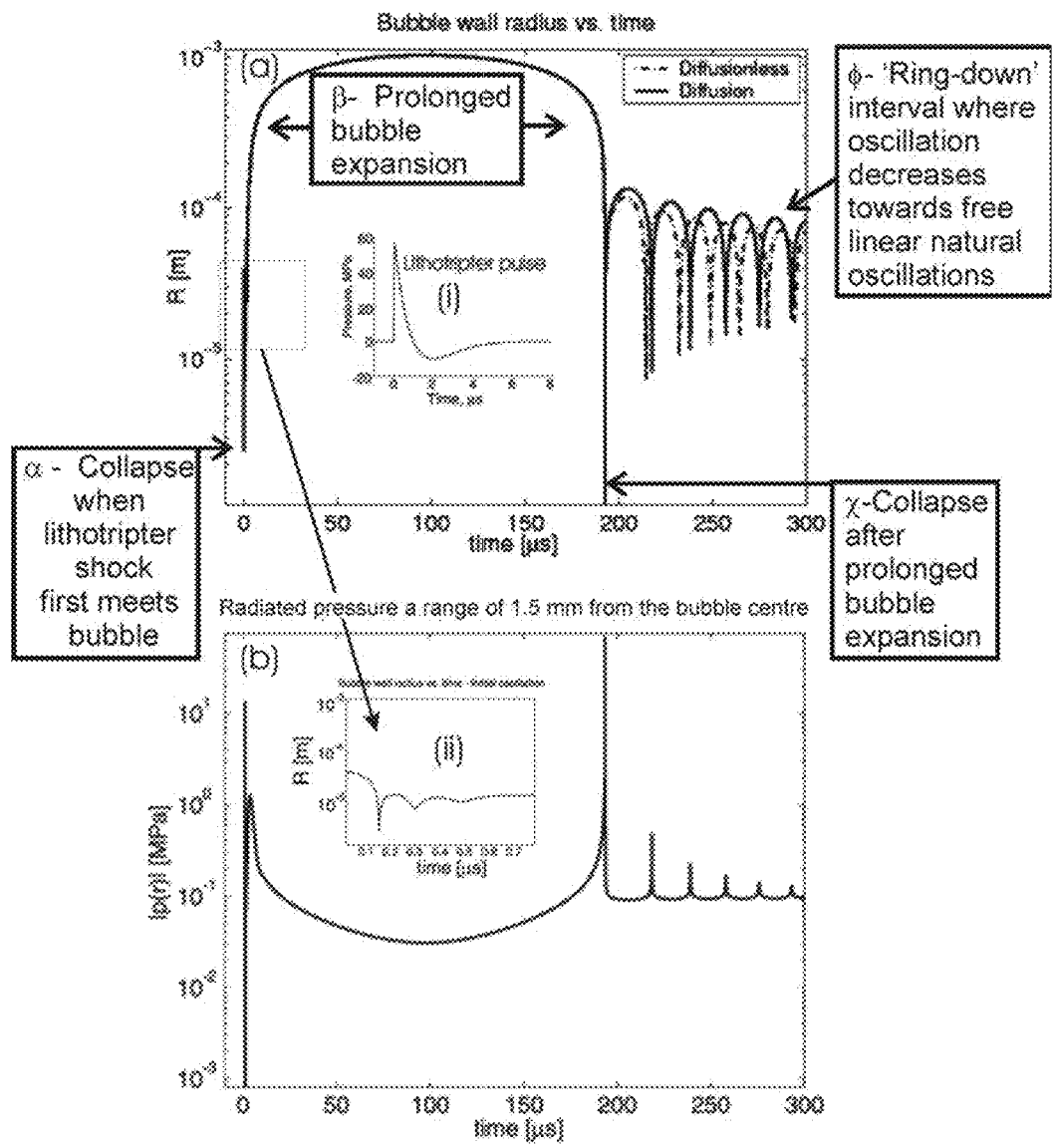
FIG. 11 is a graph showing a prediction of microbubble behaviour on exposure to a lithotripter shockwave.

In the early stages of this work, a simple and useful model interpretation of the double-peak trace was provided by comparing the passive emissions with the predictions of the Gilmore model for the behavior of a single gas bubble under such conditions. This is described for example in the papers "Acoustic emission and sonoluminuscence due to cavitation at the beam focus of an electrohydraulic shock wave lithotripter", Coleman et al., Ultrasound Med Biol 1992; 18:267-182, "Characterising in vivo acoustic cavitation during lithotripsy with time-frequency methods", Cunningham et al., Acoust Bull 2002; 26(5):10-16, and "The Acoustic Bubble, Leighton, London: Acoustic Press, 1994, the contents of which are herein incorporated by reference in their entirety. The behaviour of a bubble in the shockwave field according to this model is shown in FIG. 11. When the shockwave hits the bubble, at time 0 (approximately 50 microseconds), bubbles collapse under the high peak positive pressures in the acoustic field. As the acoustic wave passes by the bubble, the bubble experiences a region of high peak negative pressure and therefore expands. This period of expansion corresponds to time $t_c$. The bubble then undergoes inertial cavitation, or collapse, sending a blast wave towards the stone, enhancing the fragmentation started when the shockwave hit the stone. This collapse sends an acoustic emission that corresponds to $m_2$.

Cavitation experiments (as described in "The Rayleigh-like collapse of a conical bubble", Leighton et al., J Acoust Soc Am 2000; 107(1):130-142 and "What is Ultrasound?", Leighton, Progr Biophys Mol Biol 2007; 93(1-3):3-83, the contents of which are herein incorporated by reference in their entirety) and simulation (as described in "From seas to surgeries, from babbling brooks to baby scans: The acoustics of gas bubbles in liquids", Leighton, Int J Modern Phys B 2004; 18(25):3267-3314, "Free-lagrange simulations of shock/bubble interaction in shock wave lithotripsy", Jamaluddin et al., Proceedings of the Second International Conference on Computational Fluid Dynamics, ICCDF, 2002:541-546, and "Free-Lagrange simulations of the expansive and getting collapse of air bubbles in water", Turangan et al., J Fluid Mech 2008; 598:1-25, the contents of which are herein incorporated by reference in their entirety) have shown that the actual cavitational dynamics may involve complicating features not included in the Gilmore model (FIG. 11). However, these studies have also shown how useful the explanations from simple models can be. This is because, if interpreted with caution, the ensemble effect can produce features similar to those generated by the simple models. An example of this occurs if the fragmentation of a collapsing bubble is reversed by the subsequent coalescence of the fragments during the subsequent expansion phase (as described in "The Rayleigh-like collapse of a conical bubble", Leighton et al. referenced above). Based on these considerations of bubble dynamics, a simple explanation of FIGS. 9 and 11 is that the bubbles undertake a prolonged expansion phase through much of the interval $t_c$. This expansion phase is terminated by cavitational collapse and a rebound, such that the peak $m_2$ corresponds to a pressure wave generated at that rebound. Hence, a long interval $t_c$ might be interpreted as evidence of pronounced inertial cavitation provided that it is clearly terminated by a large second peak (with strong $m_2$). This is described in "The development of a passive acoustic device for monitoring the effectiveness of shockwave lithotripsy in real time", Leighton et al., *Hydroacoustics*, 11, 2008, 159-180, the contents of which are herein incorporated by reference in their entirety.

Clearly, the physical interpretation of these parameters suggests that $m_1$, $m_1$, and $t_c$ are not entirely independent. Poor targeting may cause a low value of $m_1$, just as the noise produced when a hammer 'misses' it's target will be quieter than a noise produced when a hammer 'hits' its target. Therefore, if a 'flat' signal is detected with no peaks at all, it is likely that the shockwave missed the stone entirely. Weak cavitation will cause a low value of $m_2$ and a short $t_c$; $m_2$ emissions are secondary emissions produced by the cavitating bubbles and therefore poor cavitation will result in weak secondary emissions. In addition, weak cavitation will mean that the bubbles will expand and contract to a lesser extent, taking less time to expand before contracting, which in turn reduces $t_c$. The general principles outlined above can be used to provide warning of a number of conditions unfavorable to effective stone fragmentation. In summary, poor targeting would cause a low value of $m_1$, and also a reduced $t_c$ while weak cavitation would cause a low value of $m_2$ and also a reduced value for $t_c$. This is described in greater detail in "Clinical studies of real-time monitoring of lithotripter performance using passive acoustic sensors", Leighton et al., *Proceedings of the 2nd International Urolithiasis Research Symposium*, 2008, 256-277, the contents of which are herein incorporated by reference in their entirety.

Although $m_1$ could in principle be used to assess the targeting efficacy during a treatment by assessing the strength of the reflections, this is not practically useful. This is because the $m_1$ signal is affected by so many variables such as stone density, stone location, respiration depth of the patient and BMI of the patient that the signal will be different between different patients, different treatments of the same patient, and different stones in the same patient. Therefore, $t_c$ is used by the system of the present invention to assess the efficacy of targeting. The inventors have determined that the presence or absence of a stone in a shockwave field will influence $t_c$; if the stone is present, a longer $t_c$ will be observed. An important contribution to this comes from the fact that, at any given location where cavitation might occur in front of the stone, the duration of the tension resulting from the incident SWL pulse can be extended, and the magnitude of the tension increased. A simple explanation of this effect is based on the idea that the tensile tails of the SWL pulses in part passes twice over this region, once as the incident wave and once as the reflected wave (travelling in the opposite direction). Now as $t_c$ will increase as the energy associated with the tension increases, if the shockwave hits the stone, $t_c$ will be longer and can therefore be used to assess targeting efficacy.

Accordingly, in an embodiment, the present invention uses the parameter or characteristic $t_c$ to check for 'ineffective' shocks. For example, if the processing unit 6 has deemed a shock 'ineffective', but the $t_c$ is above a particular threshold level of >100 microseconds and therefore it is clear that the targeting is accurate, then it is possible that, for example, the stone is too hard to be shattered by the cavitation in the shockwave field. On the basis of these considerations, the ratio between $m_2$ and $m_1$ is therefore used according to the present invention to demonstrate cavitation and fragmentation, and the value of $t_c$ can be used according to the present invention to provide information concerning targeting.

Clinical Development of the System

Figures 12, 13:
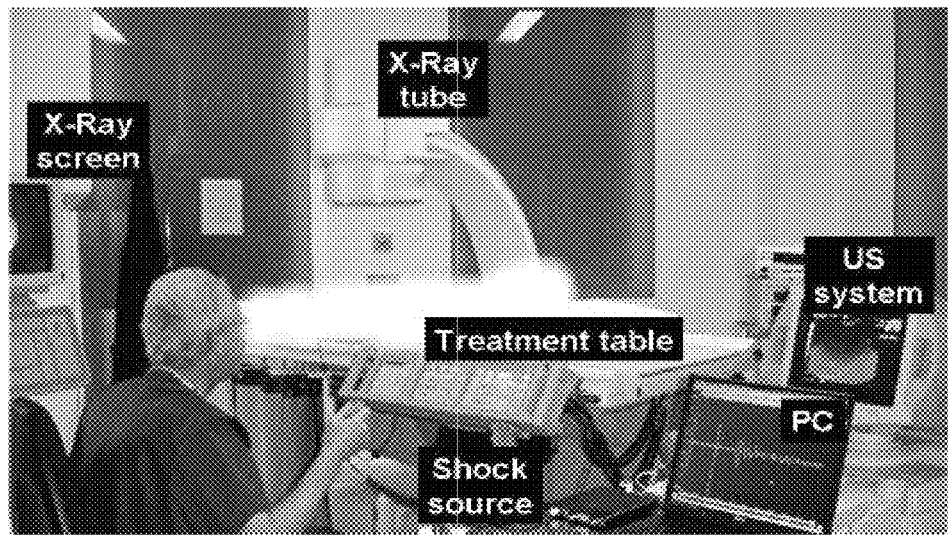
FIG. 12 is a photograph of the clinical set up for the SWL treatment, showing a 'ghosted' patient.
FIG. 13 is a table of results from one stage of development of the system, illustrating the potential of main secondary acoustic emissions characteristics to distinguish between treatments that failed and treatments that caused some stone breakage.

Alongside the preliminary development of the sensor and pre-processing unit discussed above, clinical trials of the system were also carried out, because the characteristics of the present system had to be refined and optimised for the clinical environment. FIG. 12 shows a picture of the clinical experimental set-up used in the lithotripsy theatre of Guys' Hospital according to an embodiment of the present invention. The lithotripter installed in the Day Surgery Unit is a Storz Modulith SLX-MX. This is an EM lithotripter where the operator can set an energy level, which basically controls the discharge potential of the coil. The Storz Modulith energy settings vary from 1 to 9. The most common energy level used in the treatment objects of this study was 4, which corresponds to a shock with a peak positive pressure $P^+$ of about 40 MPa and peak negative pressure $P^-$ of about 20 MPa, measured in vitro at the focus of the lithotripter. The lithotripter stone targeting and monitoring devices consist of the usual low dose X-ray fluoroscopy and ultrasound B-mode imaging systems, whose components are clearly labelled in FIG. 12.

The passive unfocused acoustic sensor 3 was placed on the side of the patient's abdomen corresponding to the side of the treated kidney. The preliminary in vitro analysis of the secondary emissions around the focus of the lithotripter showed that they were mainly generated in the proximity of the focal area of the lithotripter. That is to say, the most powerful emissions occurred in a region between the lithotripter geometrical focus (i.e. the stone) and the source. This is to be expected, given that powerful interference patterns will occur here between the reflected (from the stone) and oncoming shockwaves.

This part of the development of the signal acquisition and conditioning aspect of the present system was divided into five stages, with each stage being characterised by a different configuration of the module of data acquisition and analysis (the pre-processing unit 5). The acoustic signal was acquired by one of the three prototype ultrasound sensors developed in collaboration with PAL and supervisors. In the first three stages of the trial the signal was then directly transferred to the module of A/D conversion, a TiePie Handiscope 3 operating at a sampling frequency of 5 MHz. The oscilloscope was triggered by the electrical signal emitted by the EM at each shock. The digital signal was sent to a laptop via a USB connection.

The first stage involved 15 patients and was aimed at testing the sensitivity of the first developed multi-channel prototype sensor in vivo.

The second stage of the clinical trials was dedicated to the testing of the new single channel, round passive unfocused acoustic sensor prototype and involved 18 patients. The sensitive element in this prototype was a PVdF element whose diameter was 18 cm. A high sensitivity was observed in the magnitude of the signals acquired that were of the order of hundreds of mV. This prototype performed well in terms of SNR (at least 30%) for patients of regular weight (BMI<25). However data of good quality were obtained only from the first 5 of the 9 patients with BMI less than 25, as the sensor was at some point damaged by the lithotripter source.

Therefore in the third stage, another prototype with the same sensitivity, but a thicker protective layer, was developed. This sensor is the passive unfocused acoustic sensor according to the invention, the 'Mark III', which was tested on a set of 10 patients and similarly to the previous prototype, it could not give data of acceptable SNR for overweight patients (6 out of 10).

In the fourth stage, analogue filtering was introduced to improve the SNR before digitisation and the system was tested on two patients. One of the patients was of regular weight (BMI=23) and one was obese (BMI=32). The system still did not give a good SNR (greater than 50%) in the latter case. Therefore this stage was almost immediately followed, as mentioned hereinabove, by the introduction of signal preamplification.

Finally, in the fifth stage, both a pre-amplifier and filter were used (as illustrated in the embodiment of FIG. 1), which provided data of good SNR (greater than 50%) for all patients. This fifth stage, which involved 6 patients, was also used to analyse the features of the acoustic emissions in vivo and to compare them against treatment outcomes (the results of this stage are shown in FIG. 13 and further discussed below). A urologist, at the patient follow-up examination 2-3 weeks after the treatment, established the treatment outcomes. The results of this comparison helped the development of the signal-processing module of the diagnostic system, and in particular they were exploited to develop an interface to synchronise the operations of data acquisition with the following processing to perform on-line monitoring.

In the last two stages of the trial the signal was filtered before digitisation by an analogue high-pass filter with a cut-off frequency of about 300 kHz (specifically, 292 kHz). In the final stage, pre-amplification was also added to the signal conditioning to further increase the SNR. Sets of 30 consecutive traces were recorded at different stages of a treatment exploiting the interface of the TiePie oscilloscope and subsequently analysed off-line using MATLAB™.

Sets of at least 30 consecutive traces were recorded at different stages of the treatment. The measurement protocol was developed during the course of the preliminary clinical trials themselves, taking into account the procedure characteristics and some technical issues. These will be described below. The first aspect of the procedure that was taken into consideration was that the lithotripter operator generally used up to 200 shocks gradually to increase the energy level of the machine from 1 to the desired level for the treated patient. The operator then kept the level stable for the rest of the treatment (except for a few interruptions for monitoring), which lasted 2000-3000 shocks. The energy level influences the characteristics of the acoustic emissions. The objective of the study was to identify variations in the emissions linked exclusively to the targeting and fragmentation of the stone. Therefore it was decided to start the data acquisition once a stable energy level was reached.

A second constraint was imposed by the structure of the TiePie interface and, in particular, by the size of the saved data. The oscilloscope interface saved for each trace acquired three files of the total size of about 500 kB. The highest size of record per day compatible with the storage devices available at the time was 1 GB. The assumption was made that up to 8 treatments would be undertaken in a given day. Consequently, it was chosen to acquire 10 sets of 30 traces per treatment, spread across the duration of the treatment. That is to say, the acquisition would be started at 200 shocks and carried out every 300 shocks, with the last set of a given patient starting at 2900 shocks.

Each treatment was identified by a Treatment ID, which was an alpha-numerical code starting with the letters Lit. The datasheet also contained a section to note all the treatment details. These were the patient personal data Name, Surname, Date of birth (DOB), Weight, Height. These anagraphical details were followed by information concerning the treatment, such as the Date, any eventual information on the Stone (such as presence of single or multiple stones or the size of the stone), the stone location (Site) and the total number of Shocks administered to the patient during the treatment. Following this section with the details of the treatment, there was the data acquisition section which specified the acquisition channel (1 or 2) and the details of the different data sets recorded. For each set, note was taken of the number of Shocks already administered at the start of the set, the identification numbers of the records saved for that set (Records) and the number of shocks delivered for minute (Freq). There was also a section available to record eventual Comments (the most common was information about re-targeting) and the energy Level of the Storz EM source used when the set was recorded. The form also had a Treatment Output box, available to record the first impression on the treatment of the radiographer operating the lithotripter. Data from the clinical trials was used to build up a database of the association between different values of characteristics of the emissions and reflections and the efficacy outcomes associated with these values. The values that are known to be associated with successful treatments are then used within the processing unit as 'threshold values'. Advantageously, therefore, the inventors have developed a system and a method in which it is possible to predict the outcome of treatments based on the values of the respective signal or emission characteristics rather than known methods of looking at the value of the energy of some frequency components linked to the interactions discussed above between the stone, the incident shock wave, and the tissue (including body fluids and cavitation).

The first four stages of this clinical experimentation, which included 45 patients, were mainly devoted to the optimisation of the features of the module of data acquisition and conditioning (the sensor 3 and the pre-processing unit 5 illustrated in FIG. 1). The final configuration was tested on a further 6 patients and the data recorded in the table shown in FIG. 13. The data recorded from these further 6 patients confirmed the potential, predicted in vitro, of the main secondary acoustic emissions features ($m_1$, $m_2$, $m_2/m_1$ and $t_c$) to distinguish between treatments that failed and treatments that caused some stone breakage. For each treatment both the follow-up assessment carried out by the urologist at 2-3 weeks and the first opinion of the radiographer at the end of the treatment were reported. The specific fragmentation was not estimated for any patient at this stage, which only aimed at detecting any stone breakage. Therefore the two results columns showed either a 'B', where breakage was assessed (or supposed in the case of the first opinion), or a 'NB' for failures.

The main characteristics of the emissions were also reported with this data. Treatments that showed some stone breakage were characterised by a combination of higher collapse times $t_c$ (at least 100 µs) and higher fragmentation indices $m_2/m_1$ (0.72 and 0.43 respectively). These results were consistent with those of the in vitro experiments, which showed that long collapse times were an indication of good targeting. Collapse times measured in vivo are shorter than those measured in vitro (about 200 µs in average). Therefore the analogy between the two configurations is limited to the expectancy of a shorter collapse time in case of mistargeted stones. This situation is more likely to occur for treatments that failed, even if, as often mentioned in this thesis, targeting is not the only factor affecting a treatment. That is to say, a stone can be well on target during a whole treatment but still not break because it is too hard. In contrast, the values assumed by the fragmentation index $m_2/m_1$ in those treatments that showed some success were the same as those shown by stone phantoms at a fragmentation grade F of at least 30%. This index was clearly lower for the other treatments.

Experimentation in vitro had also showed some correlation between $m_1$, $m_2$ and $t_c$ and the fragmentation stage. Therefore it was examined whether the variations in these parameters showed any particular trend in the course of each treatment. This was done by correlating the initial shock number of the 10 stages examined per patient with the average values of the parameters at that stage. The best linear fitting of the points present in each of the three relative scattered graphs was calculated and the variation of each parameters per shock was estimated from this fitting. These estimates ($\Delta m_1/\Delta$shock, $\Delta m_2/\Delta$shock, $\Delta t_c/\Delta$shock) are also reported in FIG. 13. In accordance with in vitro experiments, most of the failed treatments showed null or small negative trends in $m_2$. However there was no substantial difference between the behaviour in the trends of $m_1$ and $t_c$ for the two sets of treatments ('B' or 'NB').

The number of patients participating in the fifth stage was not large enough to draw any statistically significant conclusions on the reliability of the system in differentiating between the two classes of treatments. However it was useful to gather information on the features of data collected in vivo that was used to develop a MATLAB™ interface that allowed on line analysis of the data. The maximum amplitude of the acoustic emissions ($m_1$) ranged from 70 mV to 477 mV and these emissions showed a delay from the electrical triggering signal (FIG. 13, Delay) that varied from a minimum of 257 μs to a maximum of 310 μs.

Further Clinical Development

Two further phases of development were carried out essentially to verify the results of the preliminary clinical trials discussed above.

Figure 14A:
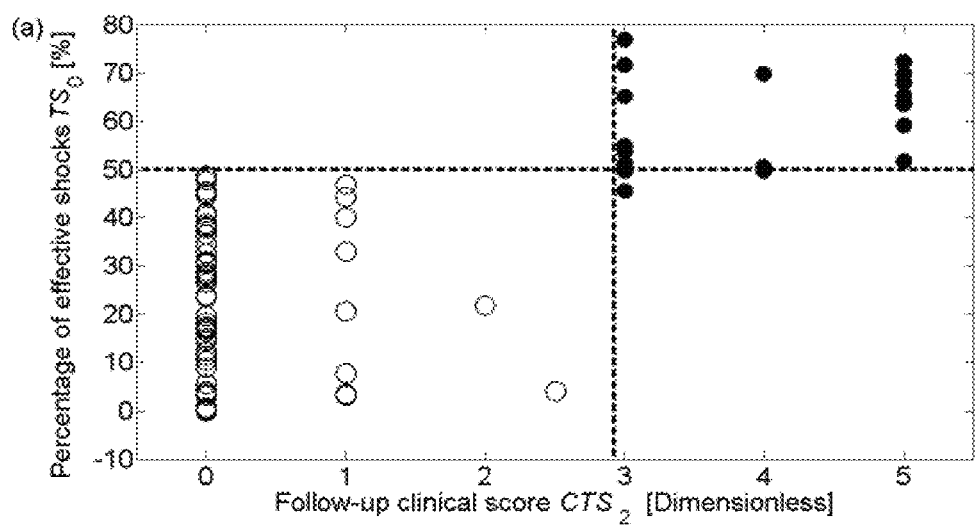
FIG. 14a is a graph showing the combined results of phase 1 and phase 2 clinical studies, comparing the results predicted by the method of the present invention with the results of a clinical X-ray follow-up assessment three weeks post-treatment.
Figure 14B:
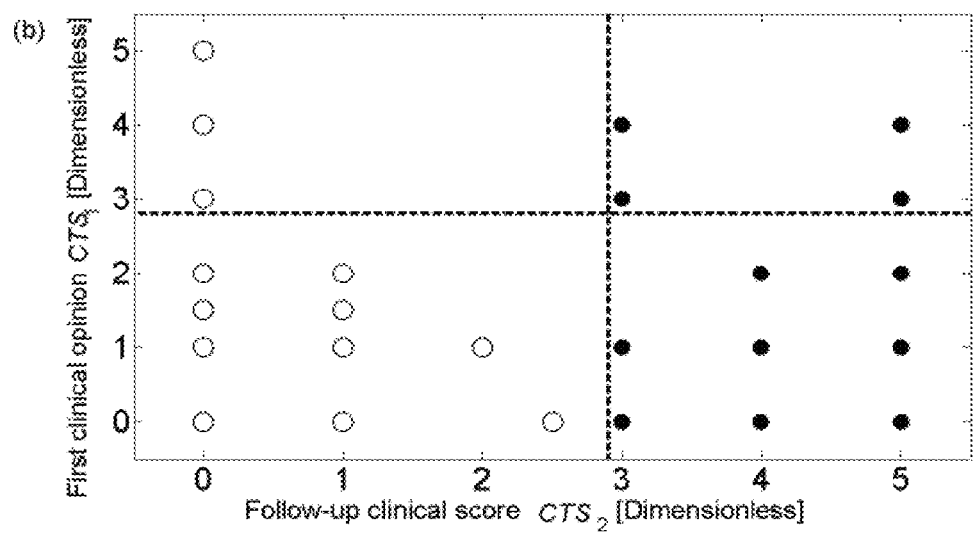
FIG. 14b is a graph showing the combined results of phase 1 and phase 2 clinical studies, comparing the results predicted by the method of the present invention with the results predicted by a clinical assessment immediately after the treatment.

FIGS. 14a and 14b show the combined results of the phase 1 and phase 2 clinical studies. Each point represents a single treatment. The abscissa of both plots A and B indicate the $CTS_2$ score, the 'gold standard' provided by the urologist at the three-week follow up assessment of stone fragmentation (based in part on x-ray analysis). Using the gold standard, the solid circles indicate 'successful' treatments ($CTS_2 \geq 3$) and the open circles indicate 'unsuccessful' treatments ($CTS_2 < 3$), a vertical dashed line showing this demarcation. Both plots contain 79 points, although fewer are visible in B because the quantification of the scoring generates overlaps. Plot A compares the treatment score from the acoustic device ($TS_0$) and $CTS_2$. The horizontal dashed line indicates the $TS_0 \geq 50\%$ delineator. Plot B does a similar comparison against $CTS_2$ but this time for the radio grapher's initial clinical treatment score, $CTS_1$. The horizontal line in B distinguishes the radiographer's estimate of successful treatments ($CTS_2 \geq 3$) from the radiographers' assessment of an unsuccessful treatment ($CTS_2 < 3$). FIG. 14a shows that the clinical trials showed the acoustic device to be successful. It plots the device-derived score $TS_0$ against the gold standards treatment score $CTS_2$. Compared with the gold standard, over the two clinical trials, the device-derived score correctly predicted the clinical effectiveness of the treatment for 78 of the 79 patients (this error occurred on a patient with a high BMI). In comparison, using the current available technology the in-theatre clinician (the radiographer) provided a treatment score $CTS_1$ which correctly predicted the outcome of only 61 of the 79 therapies (FIG. 14b). In particular, the passive acoustic device correctly predicted 18 of the 19 treatments that were successful (ie 94.7 sensitivity) whilst the current technology enabled the clinician to predict only 7 of the 19 successful treatments (ie 36.8 sensitivity).

Figure 15:
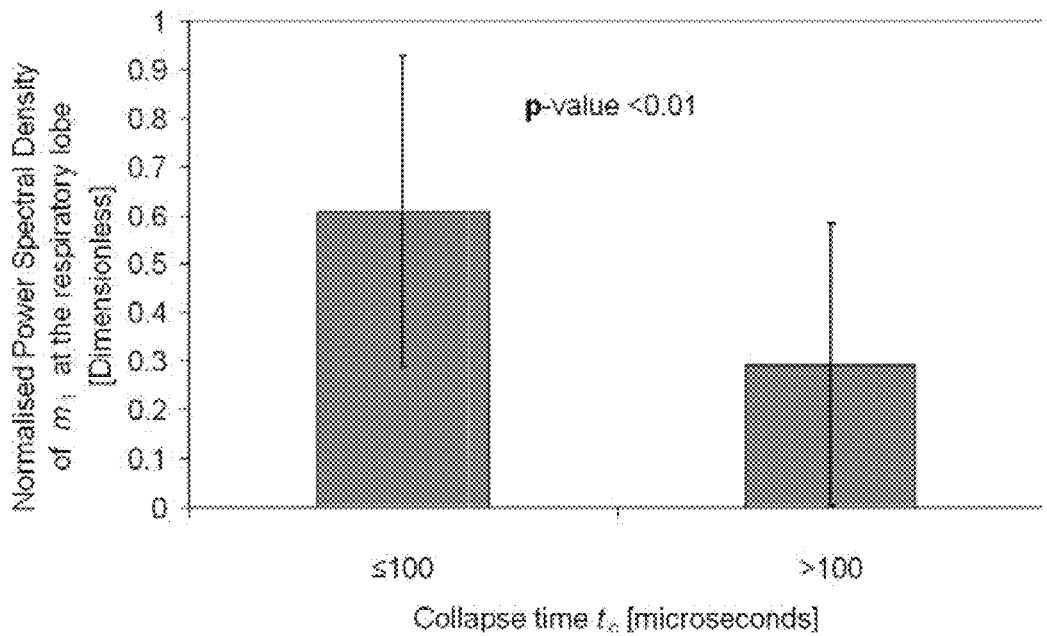
FIG. 15 is a graph showing a comparison between stone targeting achieved during deep or shallow breathing.

FIG. 15 shows a power spectral density of a 5-min clinically-acquires trace of $m_1$. It shows a lobe that is attributed to the 0.3-Hz respiration frequency lobe of the patient. The trace of $m_1$ itself is shown as an inset to the figure. The inventors have determined that the depth of respiration can be estimated from the measured characteristics of the acoustic signal, in particular the relative amplitude of the respiratory lobe. The results from both clinical studies (phases 1 and 2) were pooled to examine the level of agreement between the observation of an ineffective treatment (defined using $CTS_2$) with that arrived at if an ineffective treatment is defined as being one for which the detected respiratory lobe exceeds some threshold amplitude. The kappa value for the case when the respiratory lobe threshold is set at 50% is 0.35, indicating that a measure of respiratory depth alone using the device has some clinical use, in that deep respiration may degrade targeting. As illustrated by the graph in FIG. 15, the inventors have determined that deep breathing (represented by a high value of relative power spectral density or PSD) corresponds to relatively poor targeting (where the measured time interval value $t_c$ of the acoustic signal is less than or equal to 100 microseconds), whereas shallow breathing (represented by a low value of relative PSD) corresponds to relatively good targeting (where the measured time interval value $t_c$ is greater than 100 microseconds). Thus, the measure of respiratory depth may be used in determining whether good targeting will be achieved during the treatment of the particular patient.

Computer System

Figure 16:
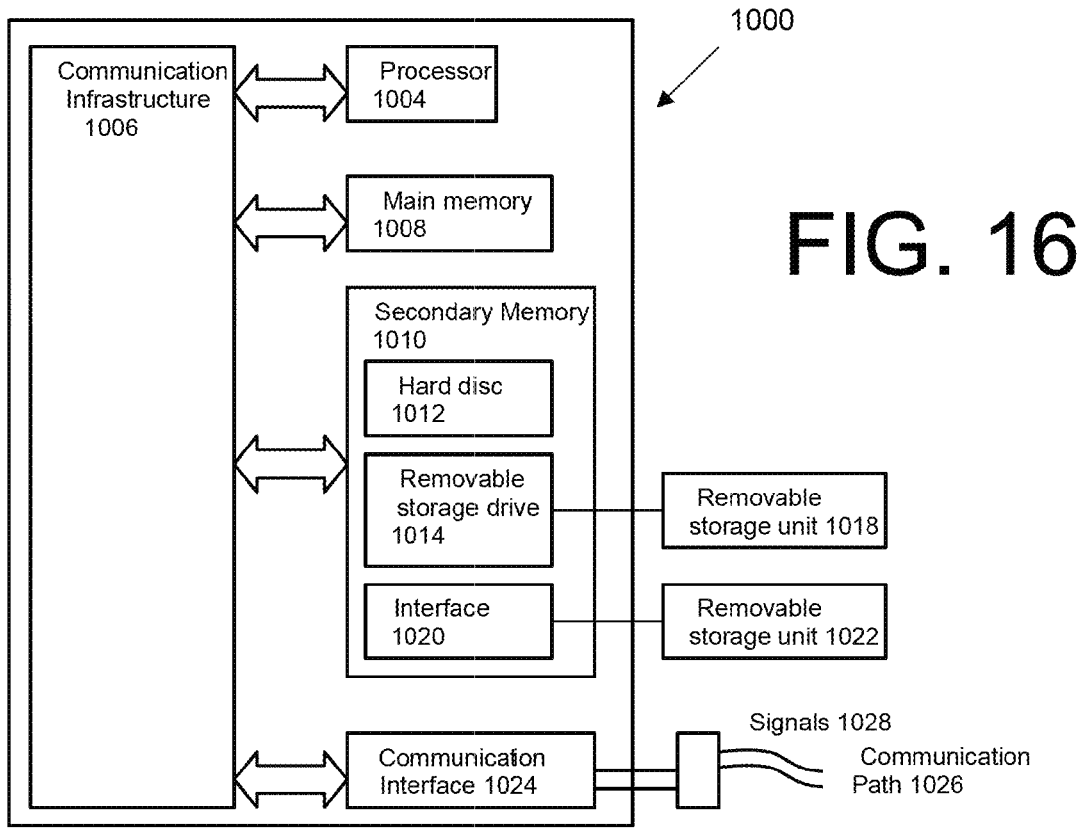
FIG. 16 is a block diagram of a computer system according to an embodiment of the present invention.

As mentioned above, the processing unit 6 may be a computer such as a computer system 1000 as shown in FIG. 16. Embodiments of the present invention may be implemented as programmable code for execution by the computer system 1000. Various embodiments of the invention are described in terms of this example computer system 1000. After reading this description, it will become apparent to a person skilled in the art how to implement the invention using other computer systems and/or computer architectures.

Computer system 1000 includes one or more processors, such as processor 1004. Processor 1004 may be any type of processor, including but not limited to a special purpose or a general-purpose digital signal processor. Processor 1004 is connected to a communication infrastructure 1006 (for example, a bus or network). Various software implementations are described in terms of this exemplary computer system. After reading this description, it will become apparent to a person skilled in the art how to implement the invention using other computer systems and/or computer architectures.

Computer system 1000 also includes a main memory 1008, preferably random access memory (RAM), and may also include a secondary memory 610. Secondary memory 1010 may include, for example, a hard disk drive 1012 and/or a removable storage drive 1014, representing a floppy disk drive, a magnetic tape drive, an optical disk drive, etc. Removable storage drive 1014 reads from and/or writes to a removable storage unit 1018 in a well-known manner. Removable storage unit 1018 represents a floppy disk, magnetic tape, optical disk, etc., which is read by and written to by removable storage drive 1014. As will be appreciated, removable storage unit 618 includes a computer usable storage medium having stored therein computer software and/or data.

In alternative implementations, secondary memory 1010 may include other similar means for allowing computer programs or other instructions to be loaded into computer system 1000. Such means may include, for example, a removable storage unit 1022 and an interface 1020. Examples of such means may include a program cartridge and cartridge interface (such as that previously found in video game devices), a removable memory chip (such as an EPROM, or PROM, or flash memory) and associated socket, and other removable storage units 1022 and interfaces 1020 which allow software and data to be transferred from removable storage unit 1022 to computer system 1000. Alternatively, the program may be executed and/or the data accessed from the removable storage unit 1022, using the processor 1004 of the computer system 1000.

Computer system 1000 may also include a communication interface 1024. Communication interface 1024 allows software and data to be transferred between computer system 1000 and external devices. Examples of communication interface 1024 may include a modem, a network interface (such as an Ethernet card), a communication port, a Personal Computer Memory Card International Association (PCM-CIA) slot and card, etc. Software and data transferred via communication interface 1024 are in the form of signals 1028, which may be electronic, electromagnetic, optical, or other signals capable of being received by communication interface 1024. These signals 1028 are provided to communication interface 1024 via a communication path 1026. Communication path 1026 carries signals 1028 and may be implemented using wire or cable, fibre optics, a phone line, a wireless link, a cellular phone link, a radio frequency link, or any other suitable communication channel. For instance, communication path 1026 may be implemented using a combination of channels.

The terms "computer program medium" and "computer usable medium" are used generally to refer to media such as removable storage drive 1014, a hard disk installed in hard disk drive 1012, and signals 1028. These computer program products are means for providing software to computer system 1000. However, these terms may also include signals (such as electrical, optical or electromagnetic signals) that embody the computer program disclosed herein.

Computer programs (also called computer control logic) are stored in main memory 1008 and/or secondary memory 1010. Computer programs may also be received via communication interface 1024. Such computer programs, when executed, enable computer system 1000 to implement the present invention as discussed herein. Accordingly, such computer programs represent controllers of computer system 1000. Where the invention is implemented using software, the software may be stored in a computer program product and loaded into computer system 1000 using removable storage drive 1014, hard disk drive 1012, or communication interface 1024, to provide some examples.

In alternative embodiments, the invention can be implemented as control logic in hardware, firmware, or software or any combination thereof. For example, the pre-processing unit 5 and the processing unit 6 may be provided in dedicated hardware circuitry which receives and processes the analog signal from the sensor 3. As those skilled in the art will appreciate, in such an alternative, it may not be necessary to include an A/D converter.

Alternatives and Modifications

In embodiments described above, the passive unfocused acoustic sensor included a piezoelectric active element and is arranged to receive passive acoustic signals and provide an analog signal representative of the detected passive acoustic signal. As those skilled in the art will appreciate, any type of sensor may instead be used, such as a fibre optic hydrophone which may provide a signal in terms of light intensity. As a further alternative, the sensor may instead include a magnetostrictive active element.

In the embodiments described above, the processing unit is arranged to check if the pre-processed data is valid by looking for null data or empty matrices, and if the data is determined to be invalid, to await reception of the next acoustic emission. As those skilled in the art will appreciate, as an alternative, the processing unit 6 may be arranged to perform additional sub-steps of determining if the data is valid, for example to look for outliers in the received data and subsequently to remove such data outliers. However, such additional processing may be undesirable as all of the received data may be important in classifying the generated shockwave.

In the embodiments described above, the characteristics of the passive acoustic signal measured are a first peak amplitude value ($m_1$), a second peak amplitude value ($m_2$) and a time interval value ($t_c$) between the first and second peak amplitude values. As those skilled in the art will appreciate, instead of determining a peak amplitude value by calculating a maximum amplitude within each burst region, alternative ways of defining the time of the centre of each peak and/or the amplitude of each peak are envisaged, for example by root mean square, centre of gravity, time averaged energy, etc. As a further alternative, those skilled in the art will appreciate that a time integrated power may be compared with a predetermined threshold, instead of a ratio of peak amplitude values. For example an integral of the square of the received signal may be calculated to determine the areas under the two bursts and a ratio of the energies of the two bursts can be compared with a predetermined threshold.

In the embodiments described above, the processing unit is arranged to monitor the treatment cycle to classify a sampled subset of generated shockwaves. As those skilled in the art will appreciate, as an alternative, it may be possible to also monitor the measured characteristics for trends, for example, to identify if the shockwaves suddenly start to fall outside the box delineated by $0.40<(m_2)/(m_1)<0.8$ and $(t_c)>100$ microseconds when previously they were within the box. In such an alternative, the processing unit may be arranged to generate an alert (which may be displayed to an operator who can then check targeting of the system) when a predetermined number (eg. 50) of consecutive sampled shocks have measured characteristics outside of the predetermined thresholds. Without such further monitoring, the treatment score TS(t) might not rapidly reflect this change in targeting accuracy because it is weighted towards a first batch (eg. 1000) of shocks for which the characteristics may generally have met the predetermined thresholds, and only slowly responds to the next 50 shocks which fall outside the box. By monitoring for trends, and generating a visual display to alert an operator when the shocks consistently fall outside of the target area, an unsuccessful treatment may be more efficiently identified and terminated prior to completion of the remaining inefficient shockwaves.

It will be understood that embodiments of the present invention are described herein by way of example only, and that various changes and modifications may be made without departing from the scope of the invention.

The invention claimed is:

1. A method for classifying a shockwave generated and directed towards a stone in an extracorporeal shockwave lithotripsy treatment, the method comprising:
   (a) receiving an acoustic signal at a passive unfocused acoustic sensor following generation of the shockwave;

(b) filtering the received acoustic signal to extract secondary acoustic emissions indicative of cavitation as a result of the shockwave generated and directed towards the stone, (c) determining, using a computer, that the filtered acoustic signal includes first and second burst regions occurring after the shockwave is generated, wherein the first and second burst regions are adjacent with a time delay therebetween;

(d) determining, using the computer, at least a first peak amplitude value (m1), a second peak amplitude value (m2), and a value (tc) corresponding to a time interval between the first and second peak amplitude values, said values (m1, m2, tc) being indicative of the degree of fragmentation and accuracy of targeting; and (e) classifying, using the computer, the shockwave as effective, if it is determined that the ratio between the second peak amplitude value (m2) and the first peak amplitude value (m1) is between predetermined threshold values and that the time interval value (tc) is greater than a predetermined threshold value.

2. A method according to claim 1, wherein the shockwave is classified as effective if it is determined that:
$0.40 < (m_2)/(m_1) < 0.8$ and
$(t_c) > 100$ microseconds.

3. A method according to claim 1, wherein the method further comprises the steps of:
transducing the received acoustic signal to an electrical signal; and
measuring a characteristic of the electrical signal.

4. A method according to claim 1, further comprising the steps of:
(i) repeating the steps of claim 1 for each of a plurality of shockwaves in the extracorporeal shockwave lithotripsy treatment;
(ii) determining a total number of 'effective' shockwaves in the treatment to give a treatment score $TS_0$; and
(iii) comparing the treatment score $TS_0$ with pre-set values to determine whether stone fragmentation has occurred.

5. A method according to claim 4, wherein a treatment score $TS_0$ value of about 50% or greater indicates stone fragmentation.

6. A method according to claim 1, further comprising
positioning the passive unfocused acoustic sensor externally on a patient's torso; and
generating a shockwave directed towards a stone.

7. A method according to claim 6, further comprising adjusting a focal point of the shockwave to closer alignment with the stone before the classifying step if the first peak amplitude values ($m_1$) for a sufficient proportion of a test dose of shockwaves do not exceed a pre-set threshold value.

8. A method according to claim 6, further comprising adjusting the focal point of the shockwave to closer alignment with the stone before the classifying step if the time interval values ($t_c$) for a sufficient proportion of a test dose of shockwaves do not exceed a pre-set threshold value.

9. A method according to claim 6, further comprising increasing the energy level of the shockwave to improve fragmentation if $t_c > 100$ microseconds but the value of $m_2$ for a sufficient proportion of a test dose of shockwaves do not exceed a pre-set threshold amplitude value.

10. A method according to claim 6, further comprising producing a figure TS(t) representing cumulative effectiveness of shockwaves during the treatment.

11. A method according to claim 6, further comprising continually monitoring the TS(t) and reducing the number of shockwaves in a treatment if the TS(t) indicates that further shockwaves are unnecessary for fragmentation.

12. A method according to claim 6, wherein the characteristics of the acoustic signal comprise a first peak amplitude value ($m_1$) of the first burst region, a second peak amplitude value ($m_2$) of the second burst region, and a time interval value ($t_c$) between the first and second peak amplitude values, the method further comprising monitoring a depth of respiration in dependence upon the measured characteristics of the acoustic signal to provide a respiratory gating signal for shockwave release.

13. A method according to claim 6, further comprising monitoring for trends in the measured characteristics of the acoustic signal and generating an alert when a change in trend is identified.

14. A system for classifying a shockwave generated and directed towards a stone in an extracorporeal shockwave lithotripsy treatment, the system comprising one or more processing units configured to:
receive an acoustic signal following generation of the shockwave directed towards a stone;
extract, from the received acoustic signal, secondary acoustic emissions indicative of cavitation as a result of the shockwave generated and directed towards the stone, and output a filtered acoustic signal;
determine that the filtered acoustic signal includes first and second burst regions occurring after the shockwave is generated, wherein the first and second burst regions are adjacent with a time delay therebetween;
determine at least a first peak amplitude value (m1), a second peak amplitude value (m2), and a value (tc) corresponding to a time interval between the first and second peak amplitude values, said values (m1, m2, tc) being indicative of the degree of fragmentation and accuracy of targeting; and
classify the shockwave as effective when it is determined that the ratio between the second peak amplitude value (m2) and the first peak amplitude value (m1) is between predetermined threshold values and that the time interval value (tc) is greater than a predetermined threshold value.

15. A non-transitory computer readable medium having instructions and data stored thereon which, when loaded into and executed by a computer, cause the computer to perform a method of classifying a shockwave generated and directed towards a stone in an extracorporeal shockwave lithotripsy treatment, the method comprising:
(a) receiving an acoustic signal at a passive unfocused acoustic sensor following generation of the shockwave;
(b) filtering the received acoustic signal to extract secondary acoustic emissions indicative of cavitation as a result of the shockwave generated and directed towards the stone, and
(c) determining that the filtered acoustic signal includes first and second burst regions occurring after the shockwave is generated, wherein the first and second burst regions are adjacent with a time delay therebetween;
(d) determining at least a first peak amplitude value (m1), a second peak amplitude value (m2), and a value (tc) corresponding to a time interval between the first and second peak amplitude values, said values (m1, m2, tc) being indicative of the degree of fragmentation and accuracy of targeting; and
(e) classifying the shockwave as effective if it is determined that the ratio between the second peak amplitude value (m2) and the first peak amplitude value (m1) is between predetermined threshold values and that the time interval value (tc) is greater than a predetermined threshold value.

16. A non-transitory computer readable medium having instructions and data stored thereon which, when loaded into and executed by a computer, cause the computer to perform a method for predicting the outcome of an Extracorporeal Shockwave Lithotripsy (SWL) treatment, the method comprising the steps of:
   (i) repeating the method of claim 1 for each shockwave in the treatment;
   (ii) determining a total number of 'effective' shockwaves in the treatment to give a treatment score $TS_0$; and
   (iii) comparing the $TS_0$ with pre-set values to determine whether stone fragmentation has occurred.

* * * * *